(12) United States Patent
Kaminsky et al.

(10) Patent No.: US 12,291,749 B2
(45) Date of Patent: ***May 6, 2025

(54) DNA METHYLATION AND GENOTYPE SPECIFIC BIOMARKER FOR PREDICTING POST-TRAUMATIC STRESS DISORDER

(71) Applicants: THE JOHNS HOPKINS UNIVERSITY, Baltimore, MD (US); UMC Utrecht Holding B.V., Utrecht (NL)

(72) Inventors: Zachary Kaminsky, Ottawa (CA); Marco Paul Maria Boks, Utrecht (NL)

(73) Assignees: The Johns Hopkins University, Baltimore, MD (US); UMC Utrecht Holding B.V., Utrecht (NL)

( * ) Notice: Subject to any disclaimer, the term of this patent is extended or adjusted under 35 U.S.C. 154(b) by 849 days.

This patent is subject to a terminal disclaimer.

(21) Appl. No.: 17/362,273

(22) Filed: Jun. 29, 2021

(65) Prior Publication Data

US 2021/0404003 A1    Dec. 30, 2021

Related U.S. Application Data

(63) Continuation of application No. 15/517,215, filed as application No. PCT/US2015/054194 on Oct. 6, 2015, now Pat. No. 11,072,828.
(Continued)

(51) Int. Cl.
*C12Q 1/68*          (2018.01)
*C07H 21/04*         (2006.01)
(Continued)

(52) U.S. Cl.
CPC ........... *C12Q 1/6883* (2013.01); *G01N 33/92* (2013.01); *C12Q 2600/118* (2013.01);
(Continued)

(58) Field of Classification Search
None
See application file for complete search history.

(56) References Cited

U.S. PATENT DOCUMENTS

| 5,786,146 A | 7/1998 | Herman et al. |
| 5,972,602 A | 10/1999 | Hyland et al. |
| (Continued) | | |

FOREIGN PATENT DOCUMENTS

| WO | 2001031580 A2 | 5/2001 |
| WO | 2008144371 A1 | 11/2008 |
| (Continued) | | |

OTHER PUBLICATIONS

Perlegen (dbSNP ss24087298, Aug. 2004). (Year: 2004).*
(Continued)

*Primary Examiner* — Jeanine A Goldberg
(74) *Attorney, Agent, or Firm* — Johns Hopkins Technology Ventures

(57) ABSTRACT

The present invention relates to the field of biomarkers. More specifically, the present invention relates to the use of biomarkers to predict post-traumatic stress disorder (PTSD). In one embodiment, a method for predicting PTSD in a subject comprises the steps of (a) measuring the DNA methylation level of a CpG dinucleotide in the 3' untranslated region of SKA2; (b) identifying the genotype at a SNP within the 3' UTR of SKA2, and (c) predicting PTSD in the subject using a prediction algorithm.

7 Claims, 13 Drawing Sheets

Specification includes a Sequence Listing.

Related U.S. Application Data

(60) Provisional application No. 62/060,503, filed on Oct. 6, 2014.

(51) Int. Cl.
    *C12Q 1/6883*     (2018.01)
    *G01N 33/92*     (2006.01)

(52) U.S. Cl.
    CPC . *C12Q 2600/154* (2013.01); *C12Q 2600/156* (2013.01); *G01N 2800/28* (2013.01); *G01N 2800/301* (2013.01); *G01N 2800/50* (2013.01); *G01N 2800/52* (2013.01); *G01N 2800/7004* (2013.01)

(56) References Cited

U.S. PATENT DOCUMENTS

| | | | |
|---|---|---|---|
| 6,033,854 | A | 3/2000 | Kurnit et al. |
| 6,180,349 | B1 | 1/2001 | Ginzinger et al. |
| 6,331,393 | B1 | 12/2001 | Laird et al. |
| 7,186,512 | B2 | 3/2007 | Martienssen et al. |
| 7,459,274 | B2 | 12/2008 | Lakey et al. |
| 7,553,627 | B2 | 6/2009 | Laird et al. |
| 7,910,296 | B2 | 3/2011 | Jeddeloh et al. |
| 7,910,880 | B2 | 3/2011 | Mukaibatake |
| 10,280,464 | B2 * | 5/2019 | Kaminsky ............ C12Q 1/6883 |
| 11,072,828 | B2 * | 7/2021 | Kaminsky ............ G01N 33/92 |
| 2002/0138208 | A1 | 9/2002 | Paulse et al. |
| 2002/0193950 | A1 | 12/2002 | Gavin et al. |
| 2003/0055615 | A1 | 3/2003 | Zhang et al. |
| 2005/0069879 | A1 | 3/2005 | Berlin |
| 2010/0009365 | A1 | 1/2010 | Laird et al. |
| 2014/0073516 | A1 | 3/2014 | Hood et al. |

FOREIGN PATENT DOCUMENTS

| | | | | |
|---|---|---|---|---|
| WO | WO-2009062134 | A1 * | 5/2009 | ........... A61K 31/497 |
| WO | WO-2011119227 | A2 * | 9/2011 | ........... A61K 31/015 |

OTHER PUBLICATIONS

Mehta et al. (PNAS, vol. 110, No. 20, pp. 8302-8307, May 14, 2013). (Year: 2013).*
Perlegen, dbSNP ss24087298, Aug. 2004.
Non-Final Office Action mailed Feb. 11, 2019 in U.S. Appl. No. 15/517,215.
Final Office Action mailed Sep. 9, 2019 in U.S. Appl. No. 15/517,215.
Final Office Action mailed Nov. 4, 2020 in U.S. Appl. No. 15/517,215.
Mehta, et al., Gene x environment vulnerability factors for PTSD: the HPA-axis. Neuropharmacology. Feb. 2012;62(2):654-62.
Pruessner, et al., Two formulas for computation of the area under the curve represent measures of total hormone concentration versus time-dependent change. Psychoneuroendocrinology. Oct. 2003;28(7):916-31.
Reijnen, et al., Prevalence of mental health symptoms in Dutch military personnel returning from deployment to Afghanistan: a 2-year longitudinal analysis. Eur Psychiatry. Feb. 2015;30(2):341-6.
Zovkic, et al., Interindividual Variability in Stress Susceptibility: A Role for Epigenetic Mechanisms in PTSD. Front Psychiatry. Jun. 26, 2013;4:60.
Sandweiss, et al., Preinjury psychiatric status, injury severity, and postdeployment posttraumatic stress disorder. Arch Gen Psychiatry. May 2011;68(5):496-504.
Schoenbaum, et al., Predictors of suicide and accident death in the Army Study to Assess Risk and Resilience in Servicemembers (Army STARRS): results from the Army Study to Assess Risk and Resilience in Servicemembers (Army STARRS). JAMA Psychiatry. May 2014;71(5):493-503.
Schubeler, et al., Function and information content of DNA methylation. Nature. Jan. 2015;517:321-326.
Sundin, et al., PTSD after deployment to Iraq: conflicting rates, conflicting claims. Psychol Med. Mar. 2010;40(3):367-82.
Thombs, et al., A validation study of the Dutch Childhood Trauma Questionnaire-Short Form: factor structure, reliability, and known-groups validity. Child Abuse Negl. Aug. 2009;33(8):518-23.
Van Zuiden, et al., Deployment-related severe fatigue with depressive symptoms is associated with increased glucocorticoid binding to peripheral blood mononuclear cells. Brain Behav Immun. Nov. 2009;23(8):1132-9.
Van Zuiden, et al., Pre-existing high glucocorticoid receptor number predicting development of posttraumatic stress symptoms after military deployment. Am J Psychiatry. Jan. 2011;168(1):89-96.
Vinkers, et al., Time-dependent changes in altruistic punishment following stress. Psychoneuroendocrinology. Sep. 2013;38(9):1467-75.
Vinkers, et al., Traumatic stress and human DNA methylation: a critical review. Epigenomics. 2015;7(4):593-608.
Vinkers, et al., Mineralocorticoid receptor haplotypes sex-dependently moderate depression susceptibility following childhood maltreatment. Psychoneuroendocrinology. Apr. 2015;54:90-102.
Witteveen, et al., Dimensionality of the posttraumatic stress response among police officers and fire fighters: an evaluation of two self-report scales. Psychiatry Res. Feb. 28, 2006;141(2):213-28.
Yehuda, et al., Hypothalamic-pituitary-adrenal dysfunction in post-traumatic stress disorder. Biol Psychiatry. Nov. 15, 1991;30(10):1031-48.
Kamali et al., (2012) Associations between suicide attempts and elevated bedtime salivary cortisol levels in bipolar disorder. J Affect Disord. Feb. 2012;136(3):350-8. doi: 10.1016/j.jad.2011.11.027. Epub Dec. 10, 2011.
Posner et al., (2011) The Columbia-Suicide Severity Rating Scale: initial validity and internal consistency findings from three multisite studies with adolescents and adults. Am J Psychiatry. Dec. 2011;168(12):1266-77. doi: 10.1176/appi.ajp.2011.10111704.
Lindqvist et al., (2008) Salivary cortisol and suicidal behavior—a follow-up study. Psychoneuroendocrinology. Sep. 2008;33(8):1061-8. doi: 10.1016/j.psyneuen.2008.05.012. Epub Jul. 30, 2008.
Lindqvist et al., (2011) CSF biomarkers in suicide attempters—a principal component analysis. Acta Psychiatr Scand. Jul. 2011;124(1):52-61. doi: 10.1111/j.1600-0447.2010.01655.x. Epub Dec. 28, 2010.
Murphy et al., (2013) Genetic variation in DNMT3B and increased global DNA methylation is associated with suicide attempts in psychiatric patients. Genes Brain Behav. Feb. 2013;12(1):125-32. doi: 10.1111/j.1601-183X.2012.00865.x. Epub Oct. 26, 2012.
Zhang et al., (2011) P11 (S100A10) as a potential biomarker of psychiatric patients at risk of suicide. J Psychiatr Res. Apr. 2011;45(4):435-41. doi: 10.1016/j.jpsychires.2010.08.012. Epub Sep. 22, 2010.
Laje et al., (2009) Genome-wide association study of suicidal ideation emerging during citalopram treatment of depressed outpatients. Pharmacogenet Genomics. Sep. 2009;19(9):666-74. doi: 10.1097/FPC.0b013e32832e4bcd.
Laje et al., (2007) Genetic markers of suicidal ideation emerging during citalopram treatment of major depression. Am J Psychiatry. Oct. 2007;164(10):1530-8.
Guintivano et al., (2013) A cell epigenotype specific model for the correction of brain cellular heterogeneity bias and its application to age, brain region and major depression. Epigenetics. Mar. 2013;8(3):290-302. doi: 10.4161/epi.23924. Epub Feb. 20, 2013.
Kellam et al., (1991) Developmental epidemiologically based preventive trials: baseline modeling of early target behaviors and depressive symptoms. Am J Community Psychol. Aug. 1991;19(4):563-84.
Kellam et al., (1994) The course and malleability of aggressive behavior from early first grade into middle school: results of a developmental epidemiologically-based preventive trial. J Child Psychol Psychiatry. Feb. 1994;35(2):259-81.
Rice et al., (2008) Identification and functional analysis of SKA2 interaction with the glucocorticoid receptor. J Endocrinol. Sep. 2008;198(3):499-509. doi: 10.1677/JOE-08-0019. Epub Jun. 26, 2008.

(56) References Cited

OTHER PUBLICATIONS

Cao et al., (2010) Intronic miR-301 feedback regulates its host gene, ska2, in A549 cells by targeting MEOX2 to affect ERK/CREB pathways. Biochem Biophys Res Commun. Jun. 11, 2010;396(4):978-82. doi: 10.1016/j.bbrc.2010.05.037. Epub May 12, 2010.

Karmakar et al., (2013) Interaction of glucocorticoid receptor (GR) with estrogen receptor (ER) α and activator protein 1 (AP1) in dexamethasone-mediated interference of ERα activity. J Biol Chem. Aug. 16, 2013;288(33):24020-34. doi: 10.1074/jbc.M113.473819. Epub Jun. 28, 2013.

Langelder et al., (2008) WGCNA: an R package for weighted correlation network analysis. BMC Bioinformatics. Dec. 29, 2008;9:559. doi: 10.1186/1471-2105-9-559.

Guintivano et al., (2013) Antenatal prediction of postpartum depression with blood DNA methylation biomarkers. Mol Psychiatry. May 2014;19(5):560-7. doi: 10.1038/mp.2013.62. Epub May 21, 2013.

Le-Niculescu et al., (2013) Discovery and validation of blood biomarkers for suicidality. Mol Psychiatry. Dec. 2013;18(12):1249-64. doi: 10.1038/mp.2013.95. Epub Aug. 20, 2013.

Rayssiguier et al., (2010) Magnesium deficiency and metabolic syndrome: stress and inflammation may reflect calcium activation. Magnes Res. Jun. 2010;23(2):73-80. doi: 10.1684/mrh.2010.0208. Epub May 31, 2010.

Bali et al., (2013) Implicating the role of plasma membrane localized calcium channels and exchangers in stress-induced deleterious effects. Eur J Pharmacol. Aug. 15, 2013;714(1-3):229-38. doi: 10.1016/j.ejphar.2013.06.010. Epub Jun. 21, 2013.

Reznikov et al., (2008) [Calcium-dependent mechanisms of stress disorders and noradrenergic responses of the hypothalamicuitary-adrenal system in neonatally androgenized female rats]. Fiziol Zh. 2008;54(6):24-9.

Nock et al., (2009) Cross-national analysis of the associations among mental disorders and suicidal behavior: findings from the WHO World Mental Health Surveys. PLoS Med. Aug. 2009;6(8):e1000123. doi: 10.1371/journal.pmed.1000123. Epub Aug. 11, 2009.

Fiori et al., (2011) Genes Brain Behav. Feb. 2013;12(1):125-32. doi: 10.1111/j.1601-183X.2012.00865.x. Epub Oct. 26, 2012. J Psychiatr Res. Sep. 2011;45(9):1229-35. doi: 10.1016/j.jpsychires.2011.03.015. Epub Apr. 17, 2011.

Shonkoff et al., (2012) The lifelong effects of early childhood adversity and toxic stress. Pediatrics. Jan. 2012;129(1):e232-46. doi: 10.1542/peds.2011-2663. Epub Dec. 26, 2011.

Turecki et al., (2012) The neurodevelopmental origins of suicidal behavior. Trends Neurosci. Jan. 2012;35(1):14-23. doi: 10.1016/j.tins 2011.11.008. Epub Dec. 15, 2011.

Balleine et al., (2010) Human and rodent homologies in action control: corticostriatal determinants of goal-directed and habitual action. Neuropsychopharmacology. Jan. 2010;35(1):48-69. doi: 10.1038/npp.2009.131.

Van Den Bos et al., (2009) The role of the ventral medial prefrontal cortex in social decision making. J Neurosci. Jun. 17, 2009;29(24):7631-2. doi: 10.1523/JNEUROSCI.1821-09.2009.

Ridder et al., (2005) Mice with genetically altered glucocorticoid receptor expression show altered sensitivity for stress-induced depressive reactions. J Neurosci. Jun. 29, 2005;25(26):6243-50.

Smalheiser et al., (2012) MicroRNA expression is down-regulated and reorganized in prefrontal cortex of depressed suicide subjects. PLoS One. 2012;7(3):e33201. doi: 10.1371/journal.pone.0033201. Epub Mar. 9, 2012.

Morlando et al., (2008) Primary microRNA transcripts are processed co-transcriptionally. Nat Struct Mol Biol. Sep. 2008;15(9):902-9.

Choi et al., (2010) Contrasting chromatin organization of CpG islands and exons in the human genome. Genome Biol. 2010;11(7):R70. doi: 10.1186/gb-2010-11-7-r70. Epub Jul. 5, 2010.

Bani-Fatemi et al., (2013) Analysis of CpG SNPs in 34 genes: association test with suicide attempt in schizophrenia. Schizophr Res. Jul. 2013;147(2-3):262-8. doi: 10.1016/j.schres.2013.04.018. Epub May 14, 2013.

Keller et al., (2011) TrkB gene expression and DNA methylation state in Wernicke area does not associate with suicidal behavior. J Affect Disord. Dec. 2011;135(1-3):400-4. doi: 10.1016/j.jad.2011.07.003. Epub Jul. 29, 2011.

Labonte et al., (2013) Genome-wide methylation changes in the brains of suicide completers. Am J Psychiatry. May 2013;170(5):511-20. doi: 10.1176/appi.ajp.2012.12050627.

Labonte et al., (2012) Differential glucocorticoid receptor exon 1(B), 1(C), and 1(H) expression and methylation in suicide completers with a history of childhood abuse. Biol Psychiatry. Jul. 1, 2012;72(1):41-8. doi: 10.1016/j.biopsych.2012.01.034. Epub Mar. 22, 2012.

Rusiecki, et al., DNA methylation in repetitive elements and post-traumatic stress disorder: a case-control study of US military service members. Epigenomics. Feb. 2012;4(1):29-40.

Solovieff, et al., Genetic Association Analysis of 300 Genes Identifies a Risk Haplotype in SLC18A2 for Post-traumatic Stress Disorder in Two Independent Samples. Neuropsychopharmacology. Jul. 2014; 39(8): 1872-1879.

Schmidt, et al., Epigenetic aspects of posttraumatic stress disorder. Dis Markers. 2011;30(2-3):77-87.

Uddin, et al., Sex differences in DNA methylation may contribute to risk of PTSD and depression: A review of existing evidence. Depress Anxiety. Dec. 2013; 30(12): 1151-1160.

Guintivano, et al., Identification and replication of a combined epigenetic and genetic biomarker predicting suicide and suicidal behaviors. Am J Psychiatry. Dec. 1, 2014;171(12):1287-96.

Mccleland, et al., Effect of site-specific modification on restriction endonucleases and DNA modification methyltransferases. Nucleic Acids Res. Sep. 1994;22(17):3640-59.

Degraves, et al., High-sensitivity quantitative PCR platform. Biotechniques. Jan. 2003;34(1):106-10, 112-5.

Deiman, et al., Characteristics and applications of nucleic acid sequence-based amplification (NASBA). Mol Biotechnol. Feb. 2002;20(2):163-79.

Gibson, et al., A novel method for real time quantitative RT-PCR. Genome Res. Oct. 1996;6(10):995-1001.

Frommer, et al., A genomic sequencing protocol that yields a positive display of 5-methylcytosine residues in individual DNA strands. Proc Natl Acad Sci U S A. Mar. 1, 1992;89(5):1827-31.

Xiong, et al., COBRA: a sensitive and quantitative DNA methylation assay. Nucleic Acids Res. Jun. 15, 1997;25(12):2532-4.

Sadri, et al., Rapid analysis of DNA methylation using new restriction enzyme sites created by bisulfite modification. Nucleic Acids Res. Dec. 15, 1996; 24(24): 5058-5059.

Eads, et al., CpG island hypermethylation in human colorectal tumors is not associated with DNA methyltransferase overexpression. Cancer Res. May 15, 1999;59(10):2302-6.

Gonzalgo, et al., Rapid quantitation of methylation differences at specific sites using methylation-sensitive single nucleotide primer extension (Ms-SNuPE). Nucleic Acids Res. Jun. 15, 1997;25(12):2529-31.

Herman, et al., Methylation-specific PCR: a novel PCR assay for methylation status of CpG islands. Proc Natl Acad Sci U S A. Sep. 3, 1996;93(18):9821-6.

Toyota, et al., Identification of differentially methylated sequences in colorectal cancer by methylated CpG island amplification. Cancer Res. May 15, 1999;59(10):2307-12.

Rein, et al., Identifying 5-methylcytosine and related modifications in DNA genomes. Nucleic Acids Res. May 15, 1998;26(10):2255-64.

Olek, et al., The pre-implantation ontogeny of the H19 methylation imprint. Nat Genet. Nov. 1997;17(3):275-6.

Ruczinski, et al. Logic Regression. Journal of Computational and Graphical Statistics. 2003;12(3):475-511.

Friedman, et al., Regularized Discriminant Analysis. J Am Stat Assoc. 1989;84(405):165-175.

Breiman, et al., Random forests. Machine Learning. Oct. 2001;45(1):5-32.

Jain, et al., Statistical Pattern Recognition: A Review. IEEE Trans Pattern Analysis Machine Intelligence. Jan. 2000;22(1):4-37.

Mouthaan, et al., The role of acute cortisol and DHEAS in predicting acute and chronic PTSD symptoms. Psychoneuroendocrinology. Jul. 2014;45:179-86.

(56) References Cited

OTHER PUBLICATIONS

Yehuda, et al., Lower methylation of glucocorticoid receptor gene promoter 1F in peripheral blood of veterans with posttraumatic stress disorder. Biol Psychiatry. Feb. 15, 2015;77(4):356-64.

Boks, et al., Longitudinal changes of telomere length and epigenetic age related to traumatic stress and post-traumatic stress disorder. Psychoneuroendocrinology. Jan. 2015;51:506-12.

Mehta, et al., Childhood maltreatment is associated with distinct genomic and epigenetic profiles in posttraumatic stress disorder. Proc Natl Acad Sci U S A. May 14, 2013;110(20):8302-7.

Sun, et al., Epigenomic association analysis identifies smoking-related DNA methylation sites in African Americans. Hum Genet. Sep. 2013;132(9):1027-37.

Birmaher, et al., Psychometric Properties of the Screen for Child Anxiety Related Emotional Disorders (SCARED): A Replication Study. J Am Acad Child Adolesc Psychiatry. Oct. 1999;38(10):1230-6.

Cox, et al., Detection of postnatal depression. Development of the 10-item Edinburgh Postnatal Depression Scale. Br J Psychiatry. Jun. 1987;150:782-6.

Cohen, et al., A global measure of perceived stress. J Health Soc Behav. Dec. 1983;24(4):385-96.

Bougea, et al., Effect of the Emotional Freedom Technique on Perceived Stress, Quality of Life, and Cortisol Salivary Levels in Tension-Type Headache Sufferers: A Randomized Controlled Trial. Explore (NY). Mar.-Apr. 2013;9(2):91-9.

Coryell, et al., The dexamethasone suppression test and suicide prediction. Am J Psychiatry. May 2001;158(5):748-53.

Mann, et al., Toward a clinical model of suicidal behavior in psychiatric patients. Am J Psychiatry. Feb. 1999;156(2):181-9.

Mcgirr, et al., Dysregulation of the sympathetic nervous system, hypothalamic-pituitary-adrenal axis and executive function in individuals at risk for suicide. J Psychiatry Neurosci. Nov. 2010;35(6):399-408.

Obradovic, et al., Biological sensitivity to context: the interactive effects of stress reactivity and family adversity on socioemotional behavior and school readiness. Child Dev. Jan.-Feb. 2010;81(1):270-89.

Deppermann, et al., Stress-induced neuroplasticity: (mal)adaptation to adverse life events in patients with PTSD—a critical overview. Neuroscience. Dec. 26, 2014;283:166-77.

Mayer, et al., Blunting of the HPA-axis underlies the lack of preventive efficacy of early post-stressor single-dose Delta-9-tetrahydrocannabinol (THC). Pharmacol Biochem Behav. Jul. 2014;122:307-18.

Bernstein, et al., Development and validation of a brief screening version of the Childhood Trauma Questionnaire. Child Abuse Negl. Feb. 2003;27(2):169-90.

Boks, et al., Investigating gene environment interaction in complex diseases: increasing power by selective sampling for environmental exposure. Int J Epidemiol. Dec. 2007;36(6):1363-9.

Bremner, et al., Psychometric properties of the Early Trauma Inventory—Self Report. J Nerv Ment Dis. Mar. 2007;195(3):211-8.

Carpenter, et al., Decreased adrenocorticotropic hormone and cortisol responses to stress in healthy adults reporting significant childhood maltreatment. Biol Psychiatry. Nov. 15, 2007; 62(10): 1080-1087.

De Kloet, et al., Assessment of HPA-axis function in posttraumatic stress disorder: pharmacological and non-pharmacological challenge tests, a review. J Psychiatr Res. Sep. 2006;40(6):550-67.

Houtepen, et al., Antipsychotic use is associated with a blunted cortisol stress response: a study in euthymic bipolar disorder patients and their unaffected siblings.

Heim, et al., Long-term neuroendocrine effects of childhood maltreatment. JAMA. Nov. 8, 2000;284(18):2321.

Hovens, et al., Self-rating inventory for posttraumatic stress disorder: review of the psychometric properties of a new brief Dutch screening instrument. Percept Mot Skills. Jun. 2002;94(3 Pt 1):996-1008.

Jaffe, et al., Accounting for cellular heterogeneity is critical in epigenome-wide association studies. Genome Biol. Feb. 4, 2014;15(2):R31.

Keane, et al., Mississippi Scale for Combat-Related Posttraumatic Stress Disorder: three studies in reliability and validity. J Consult Clin Psychol. Feb. 1988;56(1):85-90.

Klengel, et al., Allele-specific FKBP5 DNA demethylation mediates gene-childhood trauma interactions. Nat Neurosci. Jan. 2013;16(1):33-41.

Lovallo, et al., Lifetime adversity leads to blunted stress axis reactivity: studies from the Oklahoma Family Health Patterns Project. Biol Psychiatry. Feb. 15, 2012;71(4):344-9.

Malan-Muller, et al., Understanding posttraumatic stress disorder: insights from the methylome. Genes Brain Behav. Jan. 2014;13(1):52-68.

* cited by examiner

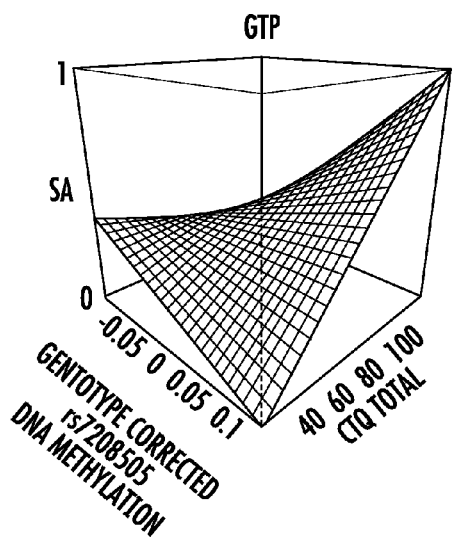
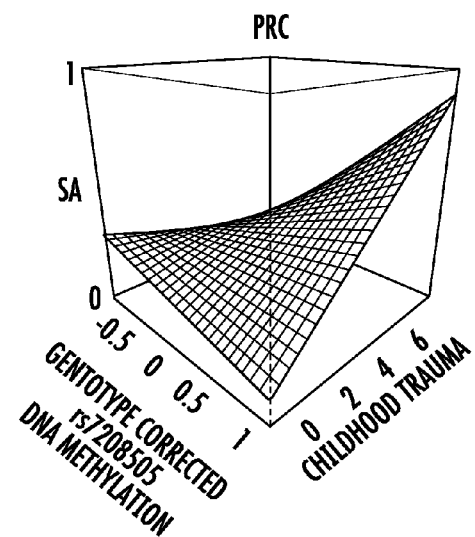
FIG. 4A    FIG. 4B
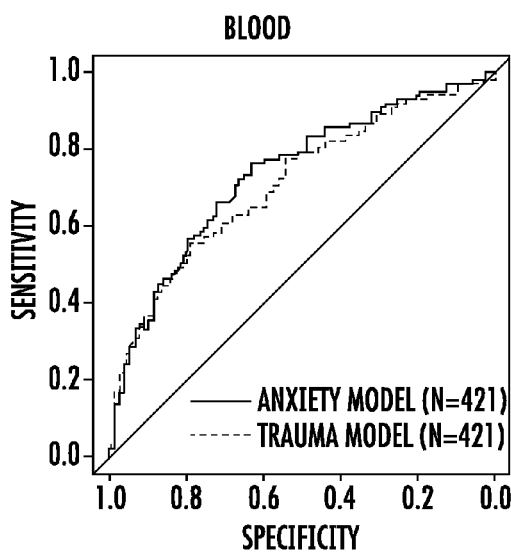
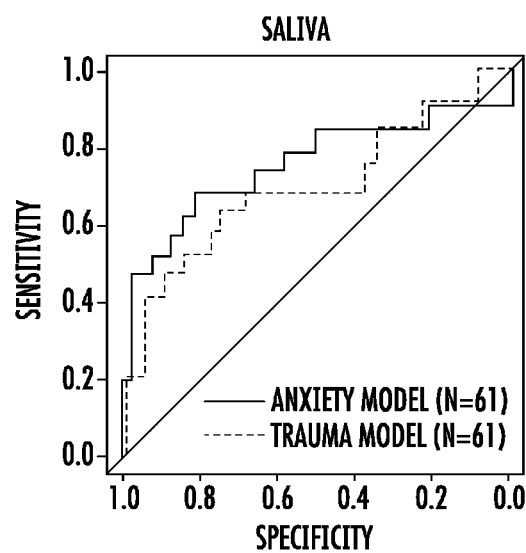
FIG. 5A    FIG. 5B

| | PTSD.T0 | PTSD.T1 | SKA2.T0 | SKA2.T1 | TRAUMA |
|---|---|---|---|---|---|
| PTSD.T1 | 0.25* | | | | |
| SKA2.T0 | 0.10 | 0.29* | | | |
| SKA2.T1 | 0.13 | 0.01 | 0.51*** | | |
| TRAUMA | 0.15 | 0.36* | 0.03 | 0.24* | |
| CHILDHOOD.TRAUMA | 0.29** | 0.48*** | 0.14 | 0.23* | 0.43*** |

FIG. 14

SEQUENCE LISTING

<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: SKA2_Fo

<400> SEQUENCE: 1
gagaaataag ttatatttta gtattagata                30

<210> SEQ ID NO 2
<211> LENGTH: 28
<212> TYPE: DNA
<213> ORGANISM: Artificial Sequence
<220> FEATURE:

<223> OTHER INFORMATION: SKA2_Ro

<400> SEQUENCE: 2
aaaataatac aatctaattt ttctccct                                28

<210> SEQ ID NO 3
<211> LENGTH: 22
<212> TYPE: DNA
<213> ORGANISM: Artificial Sequence
<220> FEATURE:
<223> OTHER INFORMATION: SKA2_Fib

<400> SEQUENCE: 3
gagatggttt tgggatgtga tg                                      22

<210> SEQ ID NO 4
<211> LENGTH: 31
<212> TYPE: DNA
<213> ORGANISM: Artificial Sequence
<220> FEATURE:
<223> OTHER INFORMATION: SKA2_Ri

<400> SEQUENCE: 4
taactaaaaa caaaaccact tttaatacta a                            31

<210> SEQ ID NO 5
<211> LENGTH: 25
<212> TYPE: DNA
<213> ORGANISM: Artificial Sequence
<220> FEATURE:
<223> OTHER INFORMATION: SKA2_Pyro

<400> SEQUENCE: 5
attataatct ctccataata ctacc                                   25

<210> SEQ ID NO 6
<211> LENGTH: 30
<212> TYPE: DNA
<213> ORGANISM: Artificial Sequence
<220> FEATURE:
<223> OTHER INFORMATION: SKA2_upstream_Fo

<400> SEQUENCE: 6
aattgttttg tttagtttga atattttaag                              30

<210> SEQ ID NO 7
<211> LENGTH: 30
<212> TYPE: DNA
<213> ORGANISM: Artificial Sequence
<220> FEATURE:
<223> OTHER INFORMATION: SKA2_upstream_Ro

<400> SEQUENCE: 7
tatctaatac taaaatataa cttatttctc                              30

<210> SEQ ID NO 8
<211> LENGTH: 24
<212> TYPE: DNA
<213> ORGANISM: Artificial Sequence
<220> FEATURE:
<223> OTHER INFORMATION: SKA2_upstream_Fib

<400> SEQUENCE: 8
tgtttaggtt ggaatgtagt ggta                                    24

```
<210> SEQ ID NO 9
<211> LENGTH: 26
<212> TYPE: DNA
<213> ORGANISM: Artificial Sequence
<220> FEATURE:
<223> OTHER INFORMATION: SKA2_upstream_Ri

<400> SEQUENCE: 9
cctaatcaaa ataataaaac cccatc                                              26

<210> SEQ ID NO 10
<211> LENGTH: 27
<212> TYPE: DNA
<213> ORGANISM: Artificial Sequence
<220> FEATURE:
<223> OTHER INFORMATION: SKA2_upstream_Pyro

<400> SEQUENCE: 10
ctctactaaa aatacaaaaa aataacc                                             27

<210> SEQ ID NO 11
<211> LENGTH: 20
<212> TYPE: DNA
<213> ORGANISM: Artificial Sequence
<220> FEATURE:
<223> OTHER INFORMATION: SKA2_Promoter_Fo1

<400> SEQUENCE: 11
gaggggaaag aaggtgtgtt                                                     20

<210> SEQ ID NO 12
<211> LENGTH: 22
<212> TYPE: DNA
<213> ORGANISM: Artificial Sequence
<220> FEATURE:
<223> OTHER INFORMATION: SKA2_Promoter_Ro1

<400> SEQUENCE: 12
ctacccaata aatctccttc ac                                                  22

<210> SEQ ID NO 13
<211> LENGTH: 20
<212> TYPE: DNA
<213> ORGANISM: Artificial Sequence
<220> FEATURE:
<223> OTHER INFORMATION: SKA2_Promoter_Fib1

<400> SEQUENCE: 13
tgaaagtaga gaggagggggg                                                    20

<210> SEQ ID NO 14
<211> LENGTH: 24
<212> TYPE: DNA
<213> ORGANISM: Artificial Sequence
<220> FEATURE:
<223> OTHER INFORMATION: SKA2_Promoter_Ri1

<400> SEQUENCE: 14
tttacactca ccatcaattc caac                                                24

<210> SEQ ID NO 15
<211> LENGTH: 19
<212> TYPE: DNA
<213> ORGANISM: Artificial Sequence
<220> FEATURE:
<223> OTHER INFORMATION: SKA2_Promoter_Pyro1
```

```
<400> SEQUENCE: 15
aatgtgtttt atgtagagg                                              19

<210> SEQ ID NO 16
<211> LENGTH: 20
<212> TYPE: DNA
<213> ORGANISM: Artificial Sequence
<220> FEATURE:
<223> OTHER INFORMATION: SKA2_Promoter_Pyro2

<400> SEQUENCE: 16
gttatttagt ttttaatggg                                             20

<210> SEQ ID NO 17
<211> LENGTH: 20
<212> TYPE: DNA
<213> ORGANISM: Artificial Sequence
<220> FEATURE:
<223> OTHER INFORMATION: SKA2_Promoter_Pyro3

<400> SEQUENCE: 17
gttgtttaat ggaggttttt                                             20

<210> SEQ ID NO 18
<211> LENGTH: 19
<212> TYPE: DNA
<213> ORGANISM: Artificial Sequence
<220> FEATURE:
<223> OTHER INFORMATION: SKA2_Promoter_PyroR4

<400> SEQUENCE: 18
cccattaaaa actaaataa                                              19

<210> SEQ ID NO 19
<211> LENGTH: 18
<212> TYPE: DNA
<213> ORGANISM: Artificial Sequence
<220> FEATURE:
<223> OTHER INFORMATION: SKA2_Promoter_PyroR5

<400> SEQUENCE: 19
aactatcact caacatct                                               18

<210> SEQ ID NO 20
<211> LENGTH: 21
<212> TYPE: DNA
<213> ORGANISM: Artificial Sequence
<220> FEATURE:
<223> OTHER INFORMATION: SKA2_Promoter_PyroR6

<400> SEQUENCE: 20
catattaaat aattaacatt c                                           21
```

DNA METHYLATION AND GENOTYPE SPECIFIC BIOMARKER FOR PREDICTING POST-TRAUMATIC STRESS DISORDER

CROSS-REFERENCE TO RELATED APPLICATIONS

This application is continuation of U.S. application Ser. No. 15/517,215, filed on Apr. 6, 2017, which is a 35 U.S.C. § 371 U.S. national entry of International Application PCT/US2015/054194, having an international filing date of Oct. 6, 2015, which claims the benefit of U.S. Provisional Application No. 62/060,503, filed Oct. 6, 2014, the content of each of the aforementioned applications is herein incorporated by reference in their entirety.

FIELD OF THE INVENTION

The present invention relates to the field of biomarkers. More specifically, the present invention relates to the use of biomarkers to predict post-traumatic stress disorder.

INCORPORATION-BY-REFERENCE OF MATERIAL SUBMITTED ELECTRONICALLY

This application contains a sequence listing. It has been submitted electronically via EFS-Web as an ASCII text file entitled "P13271-02_ST25.txt." The sequence listing is 4,056 bytes in size, and was created on Oct. 6, 2015. It is hereby incorporated by reference in its entirety.

BACKGROUND OF THE INVENTION

Post-traumatic stress disorder (PTSD) is recognized by the Department of Defense, the Department of Veterans Affairs, and the National Institute of Mental Health as a major medical issue for both deployed and returning U.S. troops. In particular, recent studies indicate that the incidence of PTSD among Iraq and Afghanistan veterans is 20% and may reach 35%, which is a rate 4-7 times higher than the general population. PTSD is not only an illness that affects military personnel; the National Institute of Mental Health (NIMH) reports that almost eight million Americans suffer from this disorder and that it ranks among the most common psychiatric conditions in the country. PTSD is characterized by diminished emotional capacity, compromised relationships with family and friends, reduced interest in activities that bring enjoyment, irritability, increased aggression, and sometimes violent behavior. Additional disorders often co-occur with PTSD, including depression, substance abuse, other anxiety disorders, anger and impulsivity disorders, and the like. Like other mental health conditions, the consequences of PTSD extend beyond the patient to their families as well. Not only are there increased long-term medical costs, there also is diminished earning capacity and adverse impacts on quality of life. In combination, these circumstances produce a cycle of spiraling demand for Federal assistance, lost earnings, and escalating, ongoing social and economic costs. Accordingly, there is a need for methods of predicting PTSD in patients.

SUMMARY OF THE INVENTION

The present invention is based, at least in part, on the discovery of a biomarker capable of predicting PTSD based on both genotype and DNA methylation status of a single CpG. The underlying biological basis for that discovery was that epigenetic and genetic variation in the 3'UTR of the SKA2 gene appeared to result in functionally relevant differences in the level to which the gene was expressed. The SKA2 protein interacts with the glucocorticoid receptor (GR) and appears to be necessary to allow the GR to enter the nucleus of a cell after it has been bound by its ligand, cortisol, or other glucocorticoid analogues. Thus, SKA2 is important for the normal functioning of the GR. Numerous data demonstrates that the ability of the GR to properly transactivate into the nucleus is important for cortisol suppression and normal regulation of the hypothalamic pituitary adrenal (HPA) axis, which is the stress response system. In suicide, data implicates an inability of this system to properly shut down in response to stress; however, in PTSD, this system may function in an opposite manner. PTSD, therefore, has a hyporeactive HPA axis response as opposed to a hyper reactive response, as is observed in suicidal behaviors. We reasoned that SKA2 epigenetic and genetic variation important for HPA axis function may therefore be informative for PTSD phenotypes. We investigated DNA methylation and rs7208505 genotype status in peripheral blood from 60 Dutch soldiers who would and 60 soldiers who would not develop PTSD. DNA methylation was sampled at two time points, pre-deployment, and after deployment to active engagement. We used the statistical model generated from the Prevention Research Center cohort as we published previously as a training set and attempted a cross validation of PTSD status in the Dutch Military sample. Modelling PTSD status developed post deployment as a function of the change in SKA2 DNA methylation, with rs7208505 genotype and age as additive covariates demonstrated an area under the receiver operator characteristic curve (AUC) of 0.78, suggesting we predicted PTSD status with 78% accuracy (FIG. 1). Subsequent linear modeling suggested that a change in SKA2 DNA methylation was adaptive to stress in the non-PTSD group, but that individuals suffering PTSD failed to demonstrate an adaptive SKA2 methylation, and thus HPA axis response. Cumulatively, the data suggest that in certain embodiments, the prediction of PTSD risk by assessing DNA methylation prior to and after a stressful event will predict the development of PTSD.

Accordingly, in one aspect, the present invention provides methods for predicting PTSD. In particular embodiments, the methods of the present invention can be administered to individuals at perceived risk who have experienced any sort of trauma including, but not limited to, military service men and women, for example, during basic training. In one embodiment, a method for predicting PTSD in a subject comprising the steps of (a) measuring the DNA methylation level of a CpG located on the minus strand of chromosome 17, at position 57187729, from DNA isolated from a sample collected from the subject; (b) identifying the genotype at the single nucleotide polymorphism (SNP), rs7208505, from DNA isolated from a sample collected from the subject; and (c) predicting PTSD in the subject using a linear model that utilizes the DNA methylation level, genotype at rs7280505, age and sex. In a further embodiment, the linear model further utilizes a stress/anxiety metric. The method can also comprise the step of generating a report displaying the methylation level, genotype and/or results from the modelling step. A report can also provide information as to potential treatment and/or recommended monitoring and/or follow-up. Alternatively, the method can further comprise the step of recommending, prescribing, or administering a PTSD treatment. In further embodiment, a method can further comprise recommending or indicating further monitoring of the subject.

In another specific embodiment, a method for predicting PTSD in a subject comprising the steps of (a) measuring the DNA methylation level of a CpG located on the minus strand of chromosome 17, at position 57187729, from DNA isolated from a sample collected from the subject; (b) identifying the genotype at the single nucleotide polymorphism (SNP), rs7208505, from DNA isolated from a sample collected from the subject; and (c) predicting PTSD in the subject using a linear model that utilizes the DNA methylation level, genotype at rs7280505, age, sex and a stress/anxiety metric.

The present invention also provides a method for predicting PTSD comprising the steps of (a) measuring DNA methylation level at a CpG dinucleotide located in the 3' untranslated region (UTR) of SKA2 from DNA isolated from a sample collected from the subject; (b) identifying the genotype at the SNP rs7208505, from DNA isolated from a sample collected from the subject; and (c) predicting PTSD in the subject using a linear model that incorporates the measured DNA methylation level and genotype. In a specific embodiment, the CpG dinucleotide in the 3' UTR of SKA2 is located on the minus strand of chromosome 17, at position 57187729. In certain embodiments, the linear model further utilizes age and sex as additive covariates. In yet another embodiment, the linear model further utilizes a stress/anxiety metric.

In a specific embodiment, the stress/anxiety metric comprises the results from a stress/anxiety questionnaire. In an alternative embodiment, the stress/anxiety metric comprises salivary cortisol measurement from the subject. In another embodiment, the stress/anxiety metric comprises a biomarker of salivary cortisol measured from the subject. The biomarker of salivary cortisol comprises CpG dinucleotide methylation at one or more loci listed in Table 8 of Guintivano et al. See Guintivano et al., 171(12) AM. J. PSYCHIATRY 1287-96 (2014).

In certain embodiments, the sample is a blood, serum, or saliva sample. In a specific embodiment, the sample is a blood, serum, or saliva sample taken before a stressor and then again after a stressor.

In particular embodiments, the DNA methylation levels are measured using polymerase chain reaction (PCR). In certain embodiments, the PCR is quantitative PCR, real-time quantitative PCR, or nested PCR. In a further embodiment, the DNA methylation levels are further measured using a sequencing assay. In certain embodiments, the measurement of DNA methylation levels can be accomplished using a primer described herein including, for example, one or more of SEQ ID NOS:1-20. A skilled artisan can design similar primers based on the disclosure provided.

In particular embodiments, CpGs within the SKA2 3'UTR, SKA2 upstream and/or SKA2 promoter regions can be used in the methods and compositions described herein. See Table 1. In a specific embodiment, PCR can be used to amplify the region of interest. In a more specific embodiment, PCR using nested primers can be used. In an even more specific embodiment, PCR primers can comprise SEQ ID NOS:11-12. In another embodiment, PCR primers can comprise SEQ ID NOS:13-14. In particular embodiments, SEQ ID NOS:11-14 can be used to amplify the SKA2 promoter region.

In another specific embodiment, PCR primers can comprise SEQ ID NOS:1-2. In another embodiment, PCR primers can comprise SEQ ID NOS:3-4. See Table 1. In particular embodiments, SEQ ID NOS:1-4 can be used to amplify the SKA2 promoter region. For SKA2 upstream, PCR primers can comprise SEQ ID NOS:6-7. Alternatively, the primers can comprise SEQ ID NOS:8-9. In further embodiments, SEQ ID NOS:6-10 can be used to amplify SKA2 upstream. See Table 1. The kit embodiments can comprise one or more of the above. Kit embodiments can comprise instructions for sample preparation, bisulfate conversion, PCR procedure/conditions, pyrosequencing and the like.

In further embodiments, sequencing can be performed using a primer shown in any one of SEQ ID NOS:15-20. In a particular embodiment, the primer shown in SEQ ID NO:18 is used. For the SKA2 3' UTR (see Table 1), SEQ ID NOS:1-2 can be used for outside PCR, SEQ ID NOS:3-4 can be used for inside PCR. In a specific embodiment, SEQ ID NO:5 can be used for sequencing. For SKA2 upstream (see Table 1), SEQ ID NOS:6-7 can be used for outside PCR, SEQ ID NOS:8-9 can be used for inside PCR. In a specific embodiment, SEQ ID NO:10 can be used for sequencing.

Accordingly, the methylation level of CpGs located within the SKA2 promoter (including the region amplified by the primers above (e.g., SEQ ID NOS:1-2, and/or SEQ ID NOS:3-4)) can be measured from DNA isolated from a sample collected from a subject. In addition, the methylation level of CpGs located upstream of the SKA2 3'UTR can be measured (including the region amplified by the primers above (e.g., SEQ ID NOS:6-7 and/or SEQ ID NOS:8-9).

In the methods of the present invention, an area under the receiver operator characteristic curve analysis can be used to predict or determining the risk of suicide attempt by the patient. In other embodiments, a linear discriminant analysis is used to predict or determining the risk of suicide attempt by the patient.

In particular embodiments, a prediction algorithm is used. In a specific embodiment, the prediction algorithm comprises a linear model. In a specific embodiment, the prediction algorithm comprises modeling PTSD risk on the DNA methylation and rs7208505 genotype prior to the onset of PTSD. In another embodiment, the prediction algorithm comprises modeling PTSD risk on the change in DNA methylation from a pre-stress time point to a time point after a stress, taking rs7208505 into the model as an additive covariate. In a more specific embodiment, the prediction algorithm comprises a linear model with DNA methylation and rs7208505 genotype modeled with an interaction with stress or anxiety metric, controlling for age and sex as additive covariates. In certain embodiments, information as it pertains to early life trauma, perceived stress, or cortisol measurements can also be used as factors in a prediction model with the DNA methylation or genetic variation to determine the risk of PTSD in the patient. In another specific embodiment, the difference in DNA methylation at SKA2 is modeled with rs7208505 as an additive covariate to predict PTSD risk.

In another aspect, the present invention provides kits useful in the methods described herein. Such kits can comprise at least one polynucleotide that hybridizes to at least one of the diagnostic biomarker sequences of the present invention and at least one reagent for detection of gene methylation. Kits can comprise any one or more of the primers shown in SEQ ID NOS:1-20. Reagents for detection of methylation include, e.g., sodium bisulfate, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein including, but not limited to, sodium bisulfite conversion, PCR procedure/conditions and/or pyrosequencing. The kit can also comprise instructions for accessing software designed to perform modeling and prediction.

The methods of the present invention can be used to evaluate patient for treatment. In certain embodiments, the present invention provides methods of treatment. In other embodiments, treatment for PTSD can include psychotherapy and/or medication. Examples of psychotherapy include, but are not limited to, cognitive therapy, exposure therapy and eye movement desensitization and reprocessing (EMDR). Medications include, but are not limited to, antidepressants, anti-anxiety medications and prazosin. Selective serotonin reuptake inhibitors (SSRIs) are type of antidepressant medication and include citalopram (Celexa), fluoxetine (Prozac), paroxetine (Paxil) and sertraline (Zoloft). In certain embodiments, PTSD treatment includes tricyclic antidepressants (amitriptyline and imipramine (Tofranil)), atypical antidepressants (mirtazapine (Remeron) and venlafaxine (Effexor), monoamine oxidase inhibitors (MAOIs) (isocarboxazid (Marplan) and phenelzine (Nardil)), mood stabilizers (carbamazepine (Tegretol) and lithium (Lithobid or Eskalith)), antipsychotics (rsiperidone (Risperdal)), and prazosin (Minipress). Thus, in particular embodiments, the present invention provides any of the above for use in a method for treating PTSD in a patient. In particular embodiments, the present invention provides any of the above medications/treatments for use in treating PTSD in a patient having the methylation and genotype described herein. The medication/treatments for use in treating PTSD in a patient can comprise assaying a sample from the patient, determining if the patient has the methylation and genotype described herein, and administering a therapeutically effective amount of a medication/treatment described herein.

BRIEF DESCRIPTION OF THE FIGURES

FIG. 4. Suicidal behavior prediction models incorporating trauma exposure. A three-dimensional depiction of the effect of the genotype corrected SKA2 3'-untranslated repeat (UTR) DNA methylation (z axis) interaction with trauma status (x axis) on suicide attempt as simulated in the (a) Grady Trauma Project (GTP) and (b) Prevention Research Study (PRC) cohorts (y axis).

FIG. 5. Receiver operator characteristic (ROC) curves of suicide attempt prediction in blood and saliva. ROC curves generated by the model generated in the Prevention Research Study (PRC) cohort and predicting suicide attempt in the GTP cohort in (a) blood and (b) saliva. The training set data from the PRC cohort was generated by a linear model of suicide attempt as a function of the interaction of SKA2 3'-UTR DNA methylation and genotype at rs7208505 with trauma scores, additively controlling for race, sex and age. Prediction in the GTP cohort input SKA2 3'-UTR DNA methylation adjusted for past substance abuse and rs7208505 genotype interacting with either total CTQ scores or anxiety (HAM-A) scores, whereas additively controlling for age and sex. CTQ, Child Trauma Questionnaire; GTP, Grady Trauma Project; UTR, untranslated repeat.

FIG. 6A. A histogram of DNA methylation at rs7208505 in the GTP cohort enabling genotype calling of N=61 subjects with missing genotype data. Dashed vertical red lines denote cut offs segregating DNA methylation inferred genotype calls using linear discriminant analysis. FIG. 6B. A boxplot of genotype calls based on microarray genotyping (y axis) as a function of genotype calls inferred by the linear discriminate analysis of genotype based on DNA methylation or DNA methylation distribution. Out of the N=360 subjects with both measures, a single outlier was detected.

FIG. 8A: SKA2 methylation changes during deployment in (non-PTSD) individuals that were exposed to either low or high levels of trauma. In individuals exposed to traumatic stress, SKA2 methylation levels increases were significantly higher (p=9.5×10−5). FIG. 8B: SKA2 methylation changes during deployment in participants that developed PTSD symptoms and those resilient to trauma. In individuals who developed PTSD symptoms after deployment, SKA2 methylation increases were significantly lower (p=6.7×10−5).

FIG. 14. Correlations (Kendall) between key variables at baseline and during follow up. PTSD.T0=PTSD symptom level at baseline; PTSD.T1=PTSD symptom level after deployment; SKA2.T0=SKA2 methylation level at baseline; SKA2.T1=SKA2 methylation level after deployment; Trauma=Trauma exposure during deployment; and Childhood.Trauma=Childhood trauma level at baseline. *$p<0.05$, $p<0.01$, *$p<0.001$.

DETAILED DESCRIPTION OF THE INVENTION

Figure 1:
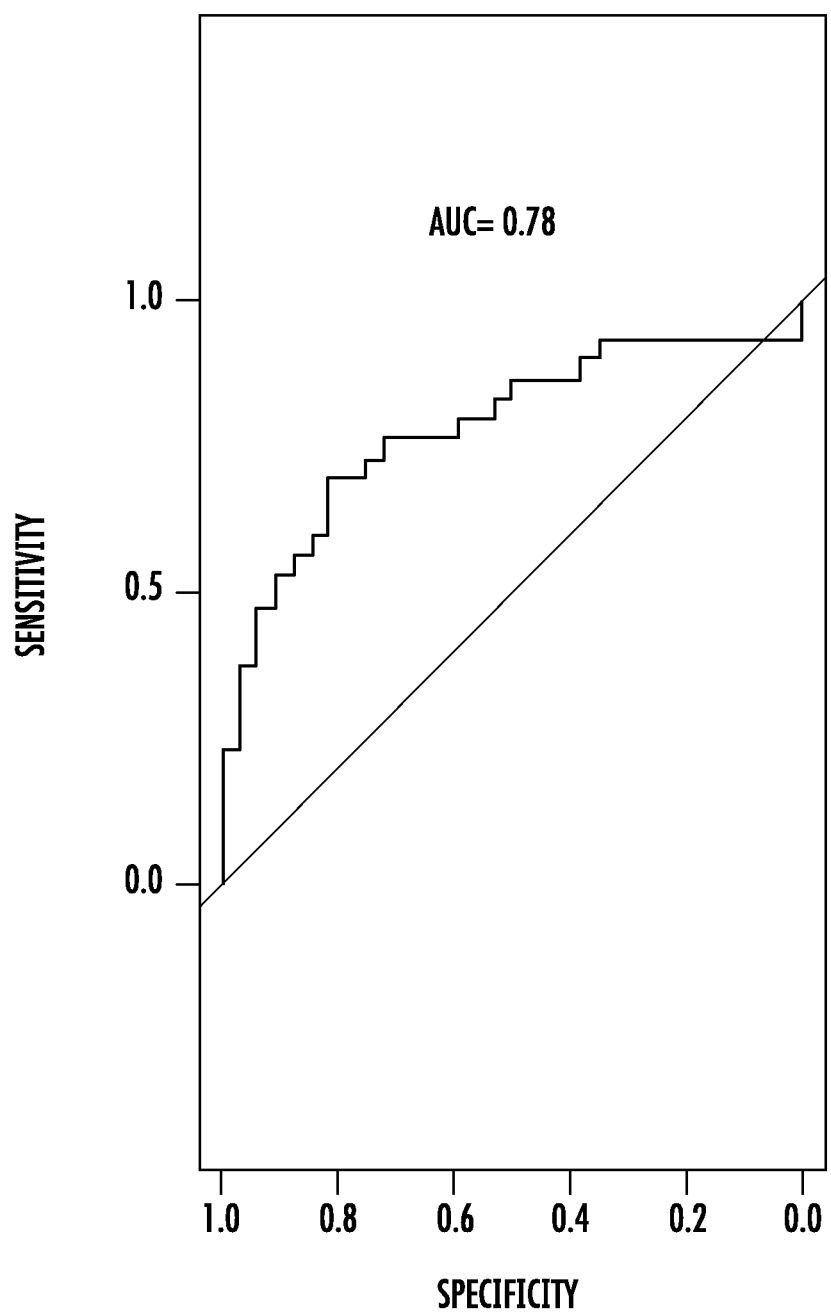
FIG. 1. The Receiver Operator Characteristic (ROC) curve demonstrating the predictive accuracy of PTSD prediction using the change in post-deployment minus pre-deployment SKA2 3'UTR DNA methylation, with rs7208505 and age as additive covariates.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

As described herein, we employed a genome-wide scan for epigenetic alterations in post mortem tissues leading to the identification of a combined genetic and epigenetic association at rs7208505 located on the 3'UTR of the spindle and kinetochore associated complex subunit 2 (SKA2) gene. We demonstrate the functional relevance of genetic and epigenetic variation to expression of the gene as well as to the production of cortisol in stressful situations. Finally, we demonstrate the predictive efficacy of statistical models generated at this locus for predicting PTSD in a pre and post deployment military cohort.

I. Definitions

As used herein, the term "comparing" refers to making an assessment of how the methylation status, proportion, level or cellular localization of one or more biomarkers in a sample from a subject relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a subject is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a subject is the same as, more or less than, different from or otherwise corresponds (or not) to the methylation status, proportion, level, or cellular localization of predefined biomarker levels that correspond to, for example, a subject at risk for PTSD, not at risk for PTSD, and the like. In a specific embodiment, the term "comparing" refers to assessing whether the methylation level of one or more biomarkers of the present invention in a sample from a subject is the same as, more or less than, different from other otherwise correspond (or not) to methylation levels of the same biomarkers in a control sample (e.g., predefined levels that correlate to subject not at risk or predicted to attempt suicide).

As used herein, the terms "indicates" or "correlates" (or "indicating" or "correlating," or "indication" or "correlation," depending on the context) in reference to a parameter, e.g., a modulated proportion, level, or cellular localization in a sample from a subject, may mean that the subject is at risk for PTSD. In specific embodiments, the parameter may comprise the methylation status or level of one or more biomarkers of the present invention. A particular set or pattern of methylation of one or more biomarkers may indicate that a subject is at risk for PTSD (i.e., correlates to a subject at risk for PTSD). In other embodiments, a particular set or pattern of methylation of one or more biomarkers may be correlated to a subject being unaffected or not at risk of PTSD. In certain embodiments, "indicating," or "correlating," as used according to the present invention, may be by any linear or non-linear method of quantifying the relationship between methylation levels of biomarkers to a standard, control or comparative value for the prediction of PTSD, assessment of efficacy of clinical treatment, identification of a subject that may respond to a particular treatment regime or pharmaceutical agent, monitoring of the progress of treatment, and in the context of a screening assay, for the identification of an anti-PTSD therapeutic.

The terms "subject," "individual," or "patient" are used interchangeably herein, and refer to a mammal, particularly, a human. The subject may have mild, intermediate or severe disease. The subject may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a subject sample and/or detecting the methylation status or level of a biomarker(s) in a sample. In one embodiment, the terms refer to obtaining a subject sample and detecting the methylation status or level of one or more biomarkers in the sample. In another embodiment, the terms "measuring" and "determining" mean detecting the methylation status or level of one or more biomarkers in a subject sample. Measuring can be accomplished by methods known in the art and those further described herein including, but not limited to, quantitative polymerase chain reaction (PCR). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a subject over time.

In particular embodiments, a biomarker would be unmethylated in a normal sample (e.g., normal or control tissue, or normal or control body fluid, stool, blood, serum, amniotic fluid), most importantly in healthy stool, blood, serum, amniotic fluid or other body fluid. In other embodiments, a biomarker would be hypermethylated in a sample from a subject having or at risk of PTSD, preferably at a methylation frequency of at least about 10%, at least about 20%, at least about 30%, at least about 40%, at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including SKA2. In more specific embodiments, a methylation profile refers to the methylation states of the 3' untranslated region (UTR) of SKA2. In even more specific embodiments, a methylation profile refers to the methylation state of CpG located on the minus strand of chromosome 17, position 57287729.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) NUCLEIC ACIDS RES. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "subject sample," "biological sample," and the like, encompass a variety of sample types obtained from a patient, individual, or subject and can be used in a diagnostic or monitoring assay. The subject sample may be obtained from a healthy subject, a subject suspected to be at risk for PTSD (family history) or a subject having a conditions associated with PTSD (e.g., depression, bipolar disorder, and the like). Moreover, a sample obtained from a subject can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or subject, e.g., a control or normal cell, organ, or subject, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a PTSD treatment (or treatment for a condition that may lead to PTSD (e.g., depression)) on a subject. In yet another embodiment, a transcription rate, mRNA level, translation rate, protein level, biological activity, cellular characteristic or property, genotype, phenotype, etc. can be determined prior to, during, or after administering a therapy into a cell, organ, or subject. In a further embodiment, a "suitable control" or "appropriate control" is a predefined value, level, feature, characteristic, property, etc. A "suitable control" can be a methylation profile of one or more biomarkers of the present invention that correlates to PTSD, to which a subject sample can be compared. The subject sample can also be compared to a negative control, i.e., a methylation profile that correlates to not at risk of PTSD.

II. Hypermethylated Biomarkers and Detection Thereof

The biomarkers of the present invention are differentially methylated in subjects at risk of PTSD versus "normal" individuals. Such biomarkers can be used individually as diagnostic tool, or in combination as a biomarker panel. In particular embodiments, the biomarkers include SKA2. In more specific embodiments, the biomarkers comprise the 3'UTR region SKA2. In even more specific embodiments, the biomarkers comprise CpG located on the minus strand of chromosome 17, position 57187729. The sequence of this biomarker is publicly available. Other biomarkers may include ATP8A1, LOC153328, and KCNAB2.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition.

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., PTSD) and thus diagnose risk or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 34(1) BIOTECHNIQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 NUCLEIC ACIDS RES. 2532-34 (1997); and Sadri & Hornsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of an unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331,393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

III. Determination of a Subject's Risk of PTSD

The present invention relates to the use of biomarkers to predict PTSD. More specifically, the biomarkers of the present invention can be used in diagnostic tests to determine the risk of or predict PTSD in an individual, subject or patient. More specifically, the biomarkers to be detected in predicting PTSD risk include SKA2. Other biomarkers known in the relevant art may be used in combination with the biomarker described herein including, but not limited to, the assessment of levels of stress hormones and their metabolites, questionnaires such as the Columbia-Suicide Severity Rating Scale, salivary cortisol levels, gene expression measures, or genetic variation deemed predictive of PTSD.

A. Biomarker Panels

The biomarkers of the present invention can be used in diagnostic tests to assess, determine, and/or qualify (used interchangeably herein) PTSD risk in a subject. The phrases "at risk of PTSD," "predictive of PTSD" and the like include any distinguishable manifestation of the risk or associated condition, including non-risk. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker of the present invention may show a statistical difference in different PTSD risks of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and individuals at risk of PTSD. In certain embodiments, the biomarkers are measured in a subject sample using the methods described herein and compared, for example, to predefined biomarker levels and correlated to PTSD risk. In particular embodiments, the measurement(s) may then be compared with a relevant diagnostic amount(s), cut-off(s), or multivariate model scores that distinguish a positive PTSD risk status from a negative PTSD risk status. The diagnostic amount(s) represents a measured amount of a hypermethylated biomarker(s) above which or below which a subject is classified as having a particular PTSD risk status. For example, if the biomarker(s) is/are hypermethylated compared to normal, then a measured amount(s) above the diagnostic cutoff(s) provides a diagnosis of PTSD risk. Alternatively, if the biomarker(s) is/are hypomethylated in a subject, then a measured amount(s) at or below the diagnostic cutoff(s) provides a diagnosis of non-PTSD risk. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from subjects with the different PTSD risk statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to predict PTSD, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of PTSD

In a specific embodiment, the present invention provides methods for determining the risk of PTSD in a subject.

Biomarker methylation percentages, amounts or patterns are characteristic of various risk states, e.g., high, medium or low. The risk of PTSD is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Subject Management

In certain embodiments of the methods of the present invention, the methods further comprise managing subject treatment based on the biomarker methylation status. Such management includes the actions of the physician or clinician subsequent to determining PTSD risk status. For example, if a physician makes a prognosis of PTSD, then a certain regime of monitoring would follow. An assessment of the risk using the methods of the present invention may then require a certain therapy regimen. Alternatively, a diagnosis of non-risk of PTSD might be followed with further testing to determine a specific disease that the subject might be suffering from. Also, further tests may be called for if the test gives an inconclusive result on PTSD risk status.

D. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a subject on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-PTSD risk profile. Therefore, one can follow the course of the methylation status of one or more biomarkers in the subject during the course of treatment. Accordingly, this method involves measuring methylation levels of one or more biomarkers in a subject receiving drug therapy, and correlating the levels with the PTSD risk status of the subject (e.g., by comparison to predefined methylation levels of the biomarkers that correspond to different PTSD risk statuses). One embodiment of this method involves determining the methylation levels of one or more biomarkers at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward PTSD risk indications.

E. Generation of Classification Algorithms for Qualifying PTSD Risk

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition or risk of PTSD.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

F. Kits for the Detection of PTSD Biomarkers

In another aspect, the present invention provides kits for qualifying PTSD risk status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Kits can comprise any one or more of the primers shown in SEQ ID NOS:1-20. Reagents for detection of methylation include, e.g., sodium bisulfate, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including SKA2. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. In particular embodiments, primers are provided that amplify all or a portion of the SKA2 3′UTR. In further embodiments, primers can be directed to the SKA2 promoter region. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including SKA2.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including SKA2.

In some embodiments, the kits comprise a methylation binding moiety and one or more polynucleotides to quantify the number of copies of at least a portion of a DNA region of a biomarker of the present invention including SKA2. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

A DNA Methylation and Genotype Specific Biomarker for Predicting Post-Traumatic Stress Disorder Materials and Methods
Human Samples.

Johns Hopkins Center for Prevention Research Study. Data are from a prospective study conducted in the context of an epidemiologically-based group-randomized prevention trial. In brief, the trial recruited two successive cohorts of students [1196 from Cohort 1 in 1985 and 1115 from Cohort 2 in 1986] as they entered first grade in 19 elementary schools in Baltimore, MD (49.8% male and 67.1% ethnic minority consistent with the population in Baltimore City schools). Since 1985, participants have been assessed through middle school, twice in young adulthood, and most recently when participants were 30-32 years old. Data for this study were derived from blood collected at the age 30-32 year follow-up wave. DNA methylation analyses were restricted to the 328 individuals participating in the age 30-32 wave who at the time of this analysis provided a blood sample (60% female and 76% African American, lacking another 12 who provided blood later). Attrition in the cohort was slightly greater among males and whites ($p<0.01$). Standardized assessments were conducted by trained non-clinical interviewers with the most recent wave collected via a computerized interview that was conducted by the interviewer, and, when assessing potentially sensitive topics such as drug involvement, conducted by the respondent using the computer). This study was approved by the Institutional Review Board at Johns Hopkins University. All participants provided informed consent to participate.

Dutch Military Sample. A samples of pre and post deployment blood was obtained from active Dutch military personnel. Of these, approximately 60 experienced PTSD post deployment and 60 did not.

Sodium Bisulfite Pyrosequencing. Bisulfite conversion was carried out using EZ DNA Methylation Gold Kit (Zymo Research, Irvine, California, USA) according to the manufacturer's instructions. Nested PCR amplifications were performed with a standard PCR protocol in 25 ml volume reactions containing 3-4 µl of sodium-bisulfate-treated DNA, 0.2 uM primers, and master mix containing Taq DNA polymerase (Sigma-Aldrich, St. Louis, Missouri, USA). Primer sequences for the SKA2 3'UTR CpG and those two CpGs analyzed upstream can be found included:

analysis. "Check" signals were accepted only in the case of failed reference sequence patterns upstream of the CpG of interest involving failure of the pyrosequencing chemistry to properly account for long runs of thymines. All data incorporated into analyses demonstrated proper bisulfite conversion based on internal pyrosequencing assay checks of cytosines not located within CpG dinucleotides.

Study Metrics. Suicidal ideation, anxiety, and stress metrics were obtained through different scales per cohort. For the PRC cohort, all metrics were derived as responses to a standardized interview. Mouthan et al., 45 PSYCHONEUROENDOCRINOLOGY 179-86 (2014); and Yehuda et al., BIOL. PSYCHIATRY (2014). Suicidal ideation was measured as a binary response to the question: Have you ever felt so low you thought of committing suicide?; suicide attempt was measured as a binary response to the question: Have you ever attempted suicide?; anxiety was measured as a binary response to the question: Do you consider yourself a nervous person? Following an affirmative response to the suicide attempt question, intent to die was measured as a binary response to the question: Did you intent to die?

For the Dutch military sample, all subjects were evaluated with The Self-Rating Inventory for PTSD at both time points.

Statistical Analysis. Unless otherwise stated, reported statistics derive from linear regression analysis, adjusted for age, sex, race, and post mortem interval (in brain cohorts) generated in R (http://www.r-project.org/). Relevant additional covariates were adjusted for if their inclusion into the model as an additive covariate caused the beta value to

TABLE 1

SKA2 pyrosequencing primer sequences

| | Primer Name | Primer Sequence 5'-3' |
|---|---|---|
| SKA2 3'UTR | SK42_Forward Outside<br>SKA2_Fo | GAGAAATAAGTTATATTTTAGTATTAGATA<br>(SEQ ID NO: 1) |
| | SK42_Reverse Outside<br>SKA2_Ro | AAAATAATACAATCTAATTTTTCTCCCT<br>(SEQ ID NO: 2) |
| | SK42_Forward Inside<br>SKA2_Fib | biotin-GAGATGGTTTTGGGATGTGATG<br>(SEQ ID NO: 3) |
| | SK42_Reverse Inside<br>SKA2_Ri | TAACTAAAAACAAAACCACTTTTAATACTA<br>(SEQ ID NO: 4) |
| | SK42_Pyrosequencing Primer<br>SKA2_Pyro | ATTATAATCTCTCCATAATACTACC<br>(SEQ ID NO: 5) |
| SKA2_upstream | SK42_upstream_Forward Outside<br>SKA2_upstream_Fo | AATTGTTTTGTTTAGTTTGAATATTTTAAG<br>(SEQ ID NO: 6) |
| | SK42_upstream_Reverse Outside<br>SKA2_upstream_Ro | TATCTAATACTAAAATATAACTTATTTCTC<br>(SEQ ID NO: 7) |
| | SK42_upstream_Forward Inside<br>SKA2_upstream_Fib | TGTTTAGGTTGGAATGTAGTGGTA<br>(SEQ ID NO: 8) |
| | SK42_upstream_Reverse Inside<br>SKA2_upstream_Ri | CCTAATCAAAATAATAAAACCCATC<br>(SEQ ID NO: 9) |
| | SK42_upstream_Pyrosequencing Primer<br>SKA2_upstream_Pyro | CTCTACTAAAAATACAAAAAAATAACC<br>(SEQ ID NO: 10) |

PCR amplicons were processed for pyrosequencing analysis according to the manufacturer's standard protocol (Qiagen, Gaithersburg, MD, USA) using a PyroMark MD system (Qiagen) with Pyro Q-CpG 1.0.9 software (Qiagen) for CpG methylation quantification. Only those data values receiving a "Pass" value or "Check" were considered for downstream change by greater than 15%. Using the Cramer-von Mises test, all data distributions that rejected the null hypothesis of normality were subsequently evaluated with non-parametric tests. All statistical tests were two tailed, $p \leq 0.05$ denotes statistical significance, and ± denotes the standard deviation. Microarray analysis employed False Discovery Rate correction for multiple testing. Where specified, genotype correction of SKA2 3'UTR DNA methylation was achieved by taking the residuals of a linear model of SKA2 3'UTR DNA methylation as a function of rs7208505 genotype. Randomization was employed within all experimental processing batches. Personnel performing laboratory experiments were blind to caseness.

Results

Figure 2:
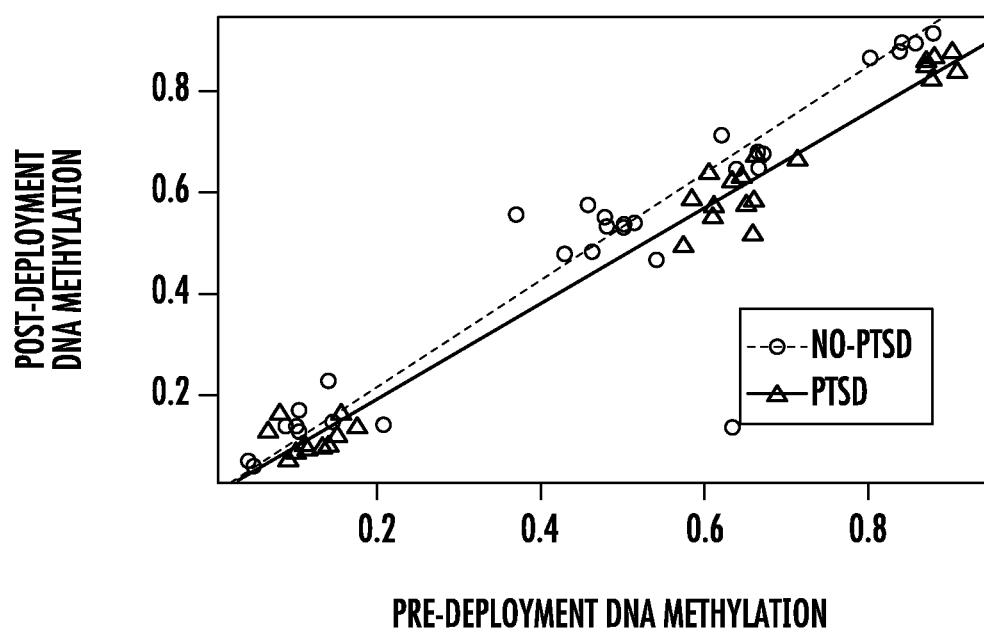
FIG. 2. A plot of the DNA methylation at the SKA2 3'UTR probe cg13989295 in Dutch soldiers at a pre (x-axis) and post (y-axis) military deployment time point. Separate plots are depicted for individuals who developed PTSD (red) and those who did not (black).

Prediction of PTSD. Identification and functional assessment of the SKA2 3'UTR locus are published previously (Guintivano et al., 171(12) AM. J. PSYCHIATRY 1287-96 (2014). We assessed the ability of our statistical model to predict PTSD in peripheral tissues of living samples. We used suicide attempt data from the PRC cohort assessed by pyrosequencing to generate an additive linear model of rs7208505 genotype and SKA2 3'UTR DNA methylation, controlling for age and sex as covariates. In the Dutch military deployment sample, we modeled the post deployment minus the pre deployment SKA2 3'UTR DNA methylation levels as measured by microarray probe values from HM450 microarray probe cg13989295. See Boks et al., 51 PSYCHONEUROENDOCRINOLOGY 506-12 (2015). The model generated an area under the receiver operator characteristic curve of 0.78 (FIG.1). A plot of the pre and post deployment DNA methylation levels in PTSD and non-PTSD individuals separately suggested that non-PTSD members appear to undergo an adaptive change in SKA2 3'UTR DNA methylation that does not occur in the PTSD individuals (FIG. 2.). Formally modeling the relationship using linear regression demonstrates this to be a highly significant relationship, accounting for 0.9768% of the variance (F-statistic: 472.5 on 5 and 56 DF, p-value: $<2.2\times10^{-16}$).

Discussion

Using previously published suicide prediction models relevant for HPA axis function[1], we assessed for the predictive efficacy of SKA2 DNA methylation for PTSD. SKA2 may influence PTSD phenotypes through its role in chaperoning the GR from the cytoplasm to the nucleus. Rice et al. demonstrated that knockdown of SKA2 eliminated GR transactivation and response to dexamethasone treatment in vitro and that protein levels of SKA2 were decreased by glucocorticoid treatment, suggesting SKA2 gene expression may be a component of the glucocorticoid feedback inhibition system. In our data, SKA2 genetic and epigenetic differences were associated with reduced suppression of salivary cortisol after waking in the GenRED cohort. As blood was not drawn at the same time as salivary cortisol sampling, the causative role of DNA methylation must be interpreted cautiously. While DNA methylation variation at rs7208505 might be important for suicidal ideation etiology, it remains possible that this variation is a reflection of cortisol variation.

While a growing number of studies are investigating epigenetic alterations in suicide, few studies report biomarkers with high prediction accuracy. To our knowledge, the identified biomarker represents the first genetic and epigenetic biomarker capable of predicting PTSD in a prospective manner with over 75%% accuracy from blood. Cumulatively, the clinical implications of this finding are that early screening of those at risk for PTSD may be possible, allowing for the identification of individuals at risk, proactive treatment, and stress and anxiety reduction. The biomarker efficacy of our findings have relevance to numerous populations, for example, the military, where the identification of an underlying vulnerability may identify those individuals at risk for developing PTSD and other co-morbid conditions when exposed to the stress of war time situations.

Example 2

Epigenetic and Genetic Variation at SKA2 Predict Suicidal Behavior and Post-Traumatic Stress Disorder Traumatic stress results in hypothalamic pituitary adrenal (HPA) axis abnormalities and an increased risk to both suicidal behaviors and post-traumatic stress disorder (PTSD). Previous work out of our laboratory identified SKA2 DNA methylation associations with suicidal behavior in the blood and brain of multiple cohorts. Interaction of SKA2 with stress predicted suicidal behavior with ~80% accuracy. SKA2 is hypothesized to reduce the ability to suppress cortisol following stress, which is of potentially high relevance in traumatized populations. Our objective was to investigate the interaction of SKA2 and trauma exposure on HPA axis function, suicide attempt and PTSD. SKA2 DNA methylation at Illumina HM450 probe cg13989295 was assessed for association with suicidal behavior and PTSD metrics in the context of Child Trauma Questionnaire (CTQ) scores in 421 blood and 61 saliva samples from the Grady Trauma Project (GTP) cohort. Dexamethasone suppression test (DST) data were evaluated for a subset of 209 GTP subjects. SKA2 methylation interacted with CTQ scores to predict lifetime suicide attempt in saliva and blood with areas under the receiver operator characteristic curve (AUCs) of 0.76 and 0.73 (95% confidence interval (CI): 0.6-0.92, P=0.003, and CI: 0.65-0.78, P<0.0001) and to mediate the suppression of cortisol following DST ($\beta=0.5\pm0.19$, F=1.51, degrees of freedom (df) =12/167, P=0.0096). Cumulatively, the data suggest that epigenetic variation at SKA2 mediates vulnerability to suicidal behaviors and PTSD through dysregulation of the HPA axis in response to stress.

Introduction

Suicide represents a major public health problem, claiming over 40 000 lives per year. Suicide rates have remained stable over the past 60 years at around 10-12 per 100 000. One strategy proposed by the National Action Alliance for Suicide Prevention to reduce the rate has been to target intervention efforts toward subgroups at the greatest risk, a strategy requiring the identification of reliable biomarkers capable of identifying those at current or future risk. Previously identified risk factors implicated in suicide include biological or genetic characteristics, early-life trauma, stressful life events, impulsive aggressive traits, psychopathology, inadequate social support, access to lethal means and substance abuse. Recent work by our group and others has identified biomarkers at the epigenetic or gene expression level capable of predicting suicidal behavior from blood.

Previous work suggests that epigenetic alterations in the spindle and kinetochore-associated protein 2 (SKA2) gene may represent a promising biomarker for detecting suicidal behaviors. This study determined that the cytosine, but not the thymine, allele of rs7208505 could be methylated and that higher DNA methylation at this site predicted lower SKA2 expression in the frontal cortex of suicide completers, along with lower levels of microRNA-301a in the cortex of depressed suicide completers. Expression of this microRNA is tied to SKA2 expression, suggesting that this observation may be a proxy of suicide-associated SKA2 decreases. Recently, Niculescu et al. demonstrated significant SKA2 expression decreases in the peripheral blood in both individuals with high suicidal ideation as well as in suicide completers relative to controls. The same group published previously on the biomarker efficacy of various peripheral blood based gene expression biomarkers9 that have also subsequently been independently replicated. Data exist to suggest that these gene systems may be linked, further implicating the possible efficacy of biomarker-based suicidal behavior prediction. An important feature of both biomarker panels is the observation of consistent associations across a broad range of suicidal behaviors including suicidal ideation, suicide attempt and suicide, suggesting that dysregulation of the gene pathways associated with these biomarkers may be an important underlying feature for the progression to increasingly severe suicidal behaviors.

SKA2 has been implicated as important for enabling glucocorticoid receptor nuclear transactivation.11 As a result, epigenetic variation influencing levels of SKA2 gene expression may be important for modulating the sensitivity of the hypothalamic pituitary adrenal (HPA) axis. A small amount of data exist to suggest that SKA2 epigenetic variation may moderate the suppression of cortisol following stress.6 Importantly, other factors known to influence the HPA axis such as early-life trauma exposure may interact with SKA2 epigenetic variation to moderate risk for suicidal behaviors. In addition, epigenetic variation at SKA2 may have relevance to other psychiatric disorders that have evidence for HPA axis system disruption such as post-traumatic stress disorder (PTSD). In this study, we used an existing data set of DNA methylation at the SKA2 3'-untranslated repeat (UTR) CpG (cg13989295) in the Grady Trauma Project cohort to investigate the effects of trauma exposure on SKA2, suicide risk and PTSD. Below, we demonstrate the effects of trauma exposure and SKA2 on suicide risk and discuss various confounding factors influencing suicide prediction efficacy.

Materials and Methods

Grady Trauma Project. The subjects for this study were part of a larger investigation of genetic and environmental factors that predict the response to stressful life events in a predominantly African American, urban population of low socioeconomic status. Research participants are approached in the waiting rooms of primary care clinics of a large, public hospital while either waiting for their medical appointments or while waiting with others who were scheduled for medical appointments. After the subjects provided written informed consent, they participated in a verbal interview and blood draw. This cohort is characterized by high rates of interpersonal violence and psychosocial stress; the majority of subjects report at least one major trauma during their lifetime, and the number of traumatic experiences in childhood and adulthood predict psychiatric symptom severity in adulthood. DNA methylation analyses were performed in N=421 subjects from the blood of whom a subset of N=61 samples were also collected and analyzed from saliva.

Johns Hopkins Center for Prevention Research Study. Data are from a prospective study conducted in a predominantly African American, urban population. Details of the trial are available elsewhere.

In brief, the trial recruited two successive cohorts of students (1196 from Cohort 1 in 1985 and 1115 from Cohort 2 in 1986) as they entered first grade in 19 elementary schools in Baltimore, MD, USA (49.8% male and 67.1% ethnic minority consistent with the population in Baltimore City schools). Since 1985, participants have been assessed through middle school, twice in young adulthood and most recently when participants were 30-32 years old. DNA methylation analyses were generated as reported previously6 and were restricted to the 326 individuals participating at the age of 30-32 data collection wave who at the time of this analysis provided a blood sample (60% female and 76% African American, lacking another 12 who provided blood later).

All participants provided informed consent to participate. All procedures were approved by the Institutional Review Board of Emory University School of Medicine and the Grady Health Systems Research Oversight Committee and by the Institutional Review Board at Johns Hopkins University, respectively. Samples were randomized and investigators were blinded to the phenotypic status during experimental data processing as reported previously. Detailed information on study sample characteristics and phenotype metrics for suicidal behavior, PTSD and trauma metrics appear in Supplementary Materials and Methods and Table 3.

Biological samples. For both Grady Trauma Project (GTP) and Prevention Research Study (PRC), whole blood was collected in ethylenediaminetetraacetic acid for genetic testing. As part of the GTP screen, saliva samples were also collected.

rs7208505 DNA methylation and genotype. SKA2 3'-UTR DNA methylation levels were determined using normalized beta values for the cg13989295 probe from the Illumina (San Diego, CA, USA) HumanMethylation450 BeadChip from data generated previously (Mehta et al., 110 Proc. Natl. Acad. Sci. USA 8302-07 (2013); and Sun et al., 132 Hum. Genet. 1027-37 (2013) in the GTP cohort (Supplementary Materials and Methods and FIG. 6). In the PRC cohort, SKA2 3'-UTR DNA methylation levels were determined by pyrosequencing and rs7208505 genotype values were determined using reverse transcription quantitative PCR as reported previously (Guintivano et al., 171 Am. J. Psychiatry 1287-96 (2014).

Dexamethasone suppression test. In the GTP cohort, whole blood was collected under fasting conditions between 0800 and 0900 hours for baseline (that is, day 1) serum cortisol measurements. A subset of 213 subjects received a low-dose dexamethasone suppression test (DST) in which they took 0.5 mg dexamethasone orally at 2300 hours, and blood was collected on the next day (that is, day 2) between 0800 and 0900 hours. Serum cortisol at both time points was measured using a commercial radioimmunoassay kit (Diagnostic Systems Laboratories, Webster, TX, USA).

Statistical analysis. Unless otherwise stated, reported statistics derive from linear regression analysis, adjusted for age, sex and race generated in R (http://www.r-project.org/) using the function lm (dependent variable~(cg13989295 beta value±rs7208505 genotype)×trauma metric+age+sex+race) where the dependent variable was current suicidal ideation, lifetime suicide attempt or the natural log of the day-2 cortisol values from the DST. Unless otherwise stated, the trauma metric for the GTP cohort was the total Child Trauma Questionnaire (CTQ) score, whereas the first Eigen vector of a principle components analysis combining reported sexual abuse and the mean frequency of emotional or physical abuse was used for the PRC cohort. Relevant additional covariates were determined according to the strategy presented in the Supplementary Materials and Methods (Table 4). Using the Anderson-Darling test, all data distributions that rejected the null hypothesis of normality were subsequently evaluated with nonparametric tests. All statistical tests were two-tailed; $P \leq 0.05$ denotes statistical significance and ± denotes the s.e.m. Where specified, genotype correction of SKA2 3'-UTR DNA methylation values was achieved by taking the residuals of a linear model of cg13989295 probe beta values as a function of the rs7208505 genotype. In a similar manner and as justified in Supplementary Materials and Methods, we adjusted SKA2 DNA methylation levels for past history of substance abuse in all receiver operator characteristic curve analyses as the availability of different substance abuse variables in the training data set precluded the ability to account for substance-related decreases on SKA2 DNA methylation.

Sliding window analyses were performed for visualization purposes, whereby subsamples were grouped such that all individuals falling within ±15 units for the CTQ total or ±5 units for CTQ emotional, sexual or physical abuse scores were included in the analysis. Differences in sliding window lengths allow for inclusion of similar sample numbers per group (mean sample size~57 per window for all analyses).

Results

Application of suicide prediction model to the GTP cohort. We aimed to predict lifetime suicide attempt using only SKA2 epigenetic and genetic variation without interacting covariates in order to assess the biomarker efficacy of the model independent of factors that may be independently associated with suicide. We assessed the model efficacy in both N=67 current suicidal ideators compared with N=337 controls and N=99 lifetime suicide attempt cases relative to N=321 controls. We observed poor predictive accuracy using the SKA2-only model that was significant for suicide attempt but not suicidal ideation (area under the receiver operator characteristic curve (AUC) SI: 0.55, 95% confidence interval (CI): 0.48-0.62, permuted P=0.15, AUC suicidal attempt (SA): 0.58, 95% CI: 0.52-0.64, permuted P=0.017). Estimation of and adjustment for individual cellular proportions did not substantially change the results of this analysis (data not shown).

Identification of trauma interaction in the GTP cohort. Our previously published model demonstrated that SKA2 3'-UTR DNA methylation significantly interacted with anxiety to moderate suicidal behavior. In the GTP cohort, the total anxiety score (HAMA) did not significantly interact with SKA2 DNA methylation to moderate suicide attempt (interaction $\beta=0.46\pm0.095$, F=5.68, degrees of freedom (df)=13/338, P=0.63); however, anxiety was independently associated with both the child ($\beta=0.13\pm0.025$, F=5.13, df=1/347, P=3.5×10−7) and lifetime trauma scores ($\beta=0.81\pm0.14$, F=32, df=1/345, P=3.3×10−8). Childhood trauma scores were more significantly associated with lifetime suicide attempt ($\beta=0.0083\pm0.001$, F=59.8, df=1/410, P=8.2×10−14) than were lifetime trauma scores ($\beta=0.0304\pm0.0066$, F=21.5, df=1/407, P=4.7×10−6).

Figure 3A:
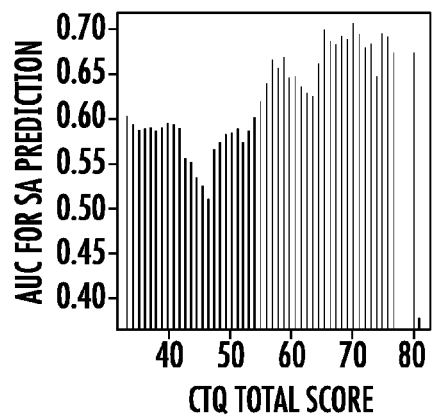
FIG. 3A-3H. Sliding window analysis of lifetime suicide attempt prediction. Barplots of the area under the receiver operator characteristic curve (AUC) generated using the suicide prediction model (y axis) as a function of childhood trauma scores. For each group (x axis), individuals are included if they fall within a window of (FIG. 3A) ±30 points on the total Child Trauma Questionnaire (CTQ) scores, (FIG. 3B) ±5 points on the emotional abuse subscale, (FIG. 3C) ±5 points on the sexual abuse subscale and (FIG. 3D) ±5 points on the physical abuse subscale from the Grady Trauma Project (GTP) cohort. Differences in sliding window lengths (±30 versus ±5) allow for inclusion of similar sample numbers per group (mean sample size ~57 per window for all analyses). Vertical red bars represent the windows where 95% confidence intervals for the AUC do not encompass a null prediction of 0.5. Barplots of the mean suicide attempt (SA) minus non-SA score generated by the suicide prediction model (y axis) as a function of the middle position of sliding window encompassing all individuals within a window of (FIG. 3E) ±30 points on the total CTQ scores and those representing only ±5 points on the (FIG. 3F) emotional abuse, (FIG. 3G) sexual abuse and (FIG. 3H) physical abuse subscales (x axis) from the GTP cohort. All vertical red bars represent those windows where 95% confidence intervals for the AUC do not encompass a null prediction of 0.5.
Figure 3B:
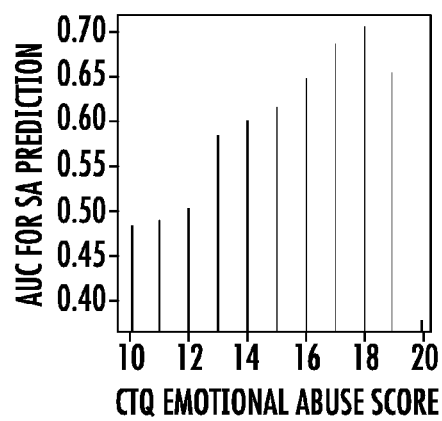
Figure 3C:
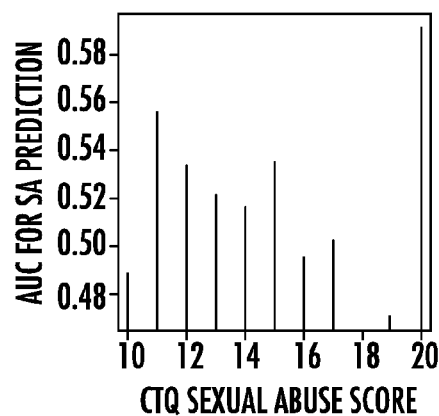
Figure 3D:
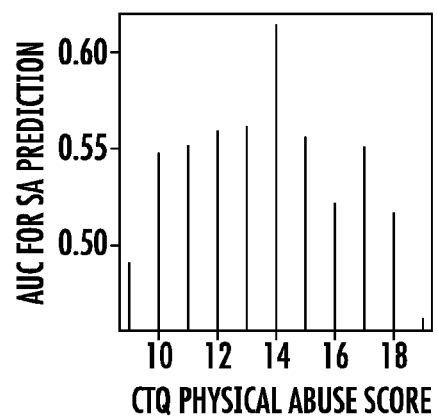
Figure 3E:
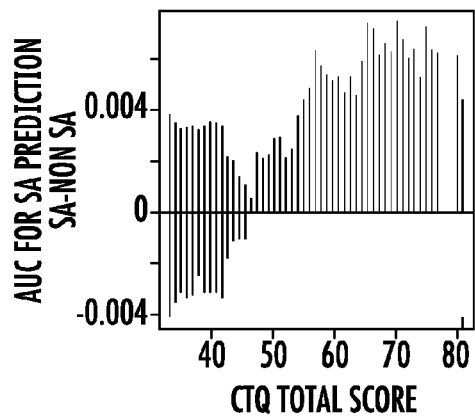
Figure 3F:
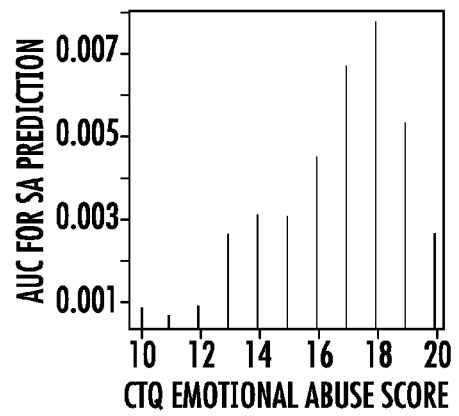
Figure 3G:
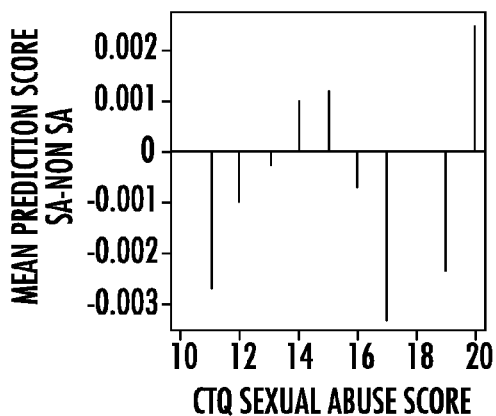
Figure 3H:
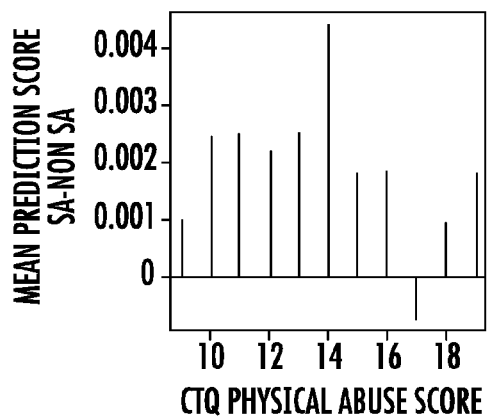

We attempted to predict lifetime suicide attempt using only SKA2 epigenetic and genetic variation without interacting covariates in subsets of individuals with different levels of child trauma exposure. We performed a sliding window analysis, generating an AUC value for suicide attempt prediction for all individuals within a range of 30 points on the CTQ. The results depicted in FIG. 3a demonstrate two peaks of maximum predictive accuracy corresponding to groups in both the high and low trauma categories. Importantly, the direction of suicide attempt prediction in both cases appears to be reversed between these low and high trauma-exposed groupings (FIG. 3e). This, in effect, cancels out the predictive efficacy of the SKA2-only model and suggests that SKA2 3'UTR DNA methylation may interact with the trauma status to moderate suicide risk. Linear regression modeling in the GTP cohort confirmed a significant interaction between CTQ total trauma scores and SKA2 DNA methylation model terms after controlling for age, sex, race and lifetime substance abuse history (Table 2, FIG. 4a). In the highly traumatized group, the maximum predictive efficacy of N=28 suicide attempt cases from N=37 non-attempters was an AUC of 0.71 (95% CI: 0.58-0.83, permuted P=0.002).

TABLE 2

Interactive Effects on Suicide Phenotypes

| Sample Model terms | β-value | Error | P-value | β-value | Error | P-value |
|---|---|---|---|---|---|---|
| | PRC suicidal ideation (N = 325) | | | PRC suicide attempt (N = 325) | | |
| DNAm | 0.002 | 0.001 | 0.19 | 0.000 | 0.001 | 0.84 |
| C/T | −0.020 | 0.064 | 0.75 | 0.036 | 0.055 | 0.51 |
| C/C | −0.17 | 0.11 | 0.11 | −0.091 | 0.094 | 0.33 |
| Trauma | 0.062 | 0.022 | 0.004 | 0.034 | 0.019 | 0.07 |
| Age | 0.003 | 0.010 | 0.74 | −0.007 | 0.009 | 0.40 |
| Sex | −0.011 | 0.052 | 0.83 | 0.001 | 0.045 | 0.98 |
| Past substance abuse | 0.10 | 0.046 | 0.027 | 0.14 | 0.040 | 0.0004 |
| DNAm × trauma | 0.002 | 0.001 | 0.020 | 0.002 | 0.001 | 0.042 |
| C/T × trauma | −0.053 | 0.045 | 0.24 | −0.083 | 0.039 | 0.035 |
| C/C × trauma | −0.19 | 0.081 | 0.019 | −0.15 | 0.070 | 0.031 |
| F | 5 | | | 2.98 | | |
| DF | 12/257 | | | 12/257 | | |
| Model R$^2$ | 0.19 | | 2.22 × 10$^{-7}$ | 0.12 | | 0.00066 |
| | GTP suicide attempt (N = 421) | | | GTP post-DST Cort (N = 209) | | |
| DNAm | −2.815 | 2.057 | 0.172 | −14.61 | 7.70 | 0.059 |
| C/T | 1.245 | 1.010 | 0.219 | 7.45 | 3.80 | 0.051 |
| C/C | 2.200 | 1.692 | 0.194 | 11.20 | 6.36 | 0.08 |
| Trauma | −0.003 | 0.004 | 0.549 | −0.029 | 0.016 | 0.084 |
| Age | 0.000 | 0.002 | 0.938 | 0.003 | 0.006 | 0.643 |
| Sex | 0.135 | 0.042 | 0.001 | −0.095 | 0.15 | 0.52 |
| Past substance abuse | 0.259 | 0.042 | 2 × 10$^{-9}$ | 0.11 | 0.16 | 0.46 |
| DNAm × trauma | 0.100 | 0.048 | 0.037$^a$ | 0.418 | 0.192 | 0.031$^a$ |
| C/T × trauma | −0.046 | 0.023 | 0.050$^a$ | −0.212 | 0.095 | 0.026$^a$ |
| C/C × trauma | −0.077 | 0.039 | 0.049$^a$ | −0.31 | 0.16 | 0.056$^a$ |
| F | 9.92 | | | 0.80 | | |

TABLE 2-continued

Interactive Effects on Suicide Phenotypes

| Sample Model terms | β-value | Error | P-value | β-value | Error | P-value |
|---|---|---|---|---|---|---|
| DF | 13/393 | | | 12/188 | | |
| Model $R^2$ | 0.25 | | $2 \times 10^{-16}$ | 0.048 | | 0.64 |

Abbreviations:
DST, dexamethasone suppression test;
GTP, Grady Trauma Project;
PRC, Prevention Research Study.
[a] Estimation of and adjustment for individual cellular proportions in the GTP cohort where these metrics were available did not substantially change the results of this analysis (data not shown).

Emotional abuse, more so than physical or sexual abuse, accounted for a majority of the total CTQ score effect on suicide attempt model predictability (FIG. 3, Supplementary Results). We next assessed model performance separately in subjects previously classified as having experienced either low or severe emotional abuse. In the severely abused group, the SKA2 epigenetic and genetic variation model predicted lifetime suicide attempt from N=51 cases compared with N=55 non-suicide attempters with an AUC of 0.695 (95% CI: 0.59-0.8, permuted P=0.005), whereas stronger associations were observed in individuals having experienced emotional but not physical or sexual abuse (Supplementary Results). In the low emotional abuse-reporting group, N=47 suicide attempters were not significantly predicted, generating an AUC of 0.56 (95% CI: 0.47-0.65, permuted P=0.23).

Replication of the interaction between SKA2 and trauma on suicidal behaviors. To corroborate the association of altered directionality of suicide ideation/attempt prediction in low versus high trauma-exposed subjects, we returned to the PRC cohort and assessed the direction of suicidal behavior prediction as a function of trauma exposure. We observed significant interactions for SKA2 3'-UTR DNA methylation and rs7208505 genotype for suicidal ideation and suicide attempt (Table 2, FIG. 4b). The strength of the interaction between trauma and SKA2 DNA methylation was strongest when modeling trauma resulting from emotional abuse as compared with physical or sexual abuse (Table 5).

Incorporation of trauma into the suicide prediction model. In light of the identified interaction of early-life trauma on suicide attempt risk, we rebuilt the statistical model from the PRC cohort, modeling the interaction of SKA2 DNA methylation and rs7208505 genotype interacting with trauma scores, adjusting for age and sex. We assessed the efficacy in both N=67 current suicidal ideators compared with N=337 controls and N=99 lifetime suicide attempt cases relative to N=321 controls, incorporating CTQ scores as the interactive covariate. Independent validation of the model in the GTP cohort predicted current SI and lifetime SA with AUCs of 0.71 and 0.73 (95% CI: 0.65-0.78, permuted P<0.0001 and CI: 0.67-0.79, permuted P<0.0001, respectively; FIG. 5a). Importantly, not adjusting SKA2 DNA methylation for substance abuse generates very similar AUCs of 0.72 and 0.72 (95% CI: 0.65-0.78, permuted P<0.0001 and CI: 0.66-0.78, permuted P<0.0001, respectively). By comparison, the predictive efficacy of past substance abuse alone at predicting suicidal ideation (SI) and SA was AUC, 0.65 and AUC, 0.67 (95% CI: 0.59-0.72, permuted P<0.0001, and CI: 0.62-0.73, permuted P<0.0001, respectively). These results generated by SKA2 interacting with trauma were very similar to those generated using anxiety (HAM-A) symptoms as the interactive covariate, generating AUCs of 0.70 and 0.70 for SI and SA (95% CI: 0.61-0.78, permuted P<0.0001 and CI: 0.64-0.77, permuted P<0.0001), respectively.

Prediction using DNA from saliva. For a subset of N=61 individuals (Table 3) from the GTP cohort, DNA methylation values generated from saliva DNA were available. A significant correlation was observed between blood-and saliva-derived SKA2 3'-UTR DNA methylation (R=0.96, P=2.2×10⁻¹⁶), suggesting that DNA obtained from salivary DNA may be efficacious for suicide behavior prediction.

We assessed the predictive efficacy of the PRC-generated model for prediction of suicidal behavior in GTP saliva samples. The AUC generated for the N=19 suicide attempters from N=42 nonattempters interacting SKA2 variation with childhood abuse scores was similar to that observed in the blood at 0.76 (95% CI: 0.6-0.92, permuted P=0.003), whereas the AUC generated interacting SKA2 with anxiety scores was 0.69 (95% CI: 0.53-0.86, permuted P=0.041; FIG. 5b). Similarly to the blood-derived data, suicidal ideation with both childhood abuse and anxiety-interacting models generated AUCs of 0.66 and 0.67 (95% CI: 0.5-0.83, permuted P=0.14 and 95% CI: 0.49-0.83, permuted P=0.11, respectively).

SKA2 interacts with childhood trauma to predict cortisol suppression following dexamethasone treatment. DNA methylation values for SKA2 were obtained on day 1 of a 2-day DST conducted in the GTP cohort. SKA2 3'-UTR DNA methylation interacted with CTQ scores to mediate the degree to which cortisol was suppressed on day 2 following the DST (Table 2, FIG. 7); however, CTQ scores alone were not associated with day-2 cortisol levels (β=0.0036±0.0038, F=0.88, df=1/203, P=0.35). Together, the data demonstrate a functional role of SKA2 DNA methylation in mediating HPA axis sensitivity. In this way, a combination of high SKA2 DNA methylation in traumatized individuals is associated with lower suppression of cortisol under stressful conditions.

Application of suicide prediction model to PTSD in GTP. Epigenetic variation at SKA2 may be efficacious for predicting PTSD, a trauma-induced disorder with HPA axis abnormalities. We therefore assessed the ability of the suicide prediction model to identify PTSD cases from the GTP cohort. Without accounting for childhood trauma, the model generated an AUC of 0.55 (95% CI: 0.48-0.63, permuted P=0.24) to identify the 78 PTSD cases from 203 controls. Genotype-adjusted DNA methylation of cg13989295 was not associated with PTSD; however, there was correlation with methylation of other SKA2 CpG sites, particularly in the promoter (Supplementary Results, Table 6, Table 7). Incorporation of CTQ scores into the model generated an AUC of 0.72 (95% CI: 0.65-0.79, permuted P<0.0001). Consistent with the literature, PTSD demonstrated a main effect of decreasing day-2 cortisol following the DST ($\beta=-1.34\pm0.58$, $F=2.17$, $df=3/121$, $P=0.021$); however, CTQ levels significantly interacted with the PTSD status to increase post-DST day-2 cortisol levels ($\beta=0.023\pm0.011$, $F=2.17$, $df=3/121$, $P=0.047$). Notably, CTQ scores were lower among individuals with PTSD and no suicide attempt compared with those with both (Wilcoxon Rank Sum: PTSD Yes, SA No: N=41, mean=51±20, PTSD Yes, SA Yes: N=37, mean=61±24, P=0.095) and higher among suicide attempters without comorbid PTSD (Wilcoxon Rank Sum: PTSD No, SA No: N=171, mean=38±14, PTSD No, SA Yes: N=32, mean=53±19, P=3.5×10-5). There was a significant overrepresentation of suicide attempters among PTSD cases (observed probability=0.47, expected probability=0.38, P=0.032). Cumulatively, the data suggest the different direction of SKA2-mediated effects on post-DST cortisol levels with CTQ scores on day 2 may be mediated by the opposing direction of PTSD and suicidal behavior on HPA axis sensitivity.

Discussion

In our previous work, we reported a relatively high predictive accuracy of the SKA2 suicide prediction model across two cohorts and identified an association between genotype-corrected DNA methylation of the SKA2 3'-UTR and neuronal SKA2 expression. This study expands upon these previous findings by assessing not only the predictive accuracy of the biomarker model in an independent and larger cohort but also the effect of the biomarker model independent of interacting covariates and detailing its performance in light of suicide risk factors such as childhood trauma. The AUC values reported above are moderate. There are a number of potential explanations for the lack of strength of the reported AUCs. First, the GTP cohort represents a primarily African American cohort, similar to the PRC cohort, with ~75% African Americans. As reported previously, the allele frequency of C-containing alleles is much smaller in this population relative to Caucasian, Asian and Native American individuals, suggesting that there may be a lower amount of biologically informative alleles capable of conferring DNA methylation information. Additional replication studies will be required in larger cohorts with more ethnic diversity to better understand the predictive efficacy of SKA2 in the general population. In addition, although our supplementary analysis did not demonstrate a confounding effect of other psychiatric illnesses, it remains possible that variation is induced by different underlying psychiatric conditions as well as different subtypes of suicidality.

Second, the predictions result from retrospective data, such that epigenetic drift over time and the confounding influence of various suicide-and trauma-associated lifestyle factors may influence the prediction. In the GTP cohort, prediction of suicide attempt metrics performed stronger than predicting suicidal ideation. Our previous data indicated that elevated SKA2 levels may be indicative of increasing severity of suicidal behaviors, which is consistent with this observation. An increased signal may be more important in a retrospective sample such as the GTP, where biological samples were taken long after a suicide attempt and factors affecting DNA methylation at SKA2 may have caused a drift in suicide-relevant signal.

Suicidal ideation, attempt, anxiety, trauma and substance abuse metrics were obtained through different scales in the GTP and PRC cohorts. Although the results in both cohorts were consistent, each has distinct clinical features that influence SKA2 methylation. This fact calls into question whether SKA2 is capable of measuring any suicide-relevant biology. In light of the findings detailing that the SKA2 epigenetic and genetic variation independent of interacting covariates was capable of similar predictive accuracies in the severe trauma cases stands as a proof of principle that SKA2 alone may act as an efficacious biomarker in certain populations, such as highly traumatized individuals.

Initial results in a small subset of DNA obtained from saliva demonstrated a similar predictive efficacy to that observed in blood. Approximately 74% of cells in the saliva are white blood cells; therefore, a high overlap between blood-and saliva-based findings is expected. It has been demonstrated that DNA derived from the saliva may be a better proxy for the epigenetic status of the brain, possibly because buccal tissue is derived from the same primary germ layer as the brain, the ectoderm. However, the relevance of peripheral biomarker signals at SKA2 to the brain have been demonstrated previously (Guintivano et al., 2014) and may result from a tissue nonspecific reprogramming of the epigenome. The implication of these observations is that salivary DNA may represent a useful collection tissue for biomarker testing, an option that would ultimately enable a less invasive and more cost-effective means to perform biomarker testing.

Our previously published model demonstrated that SKA2 3'-UTR DNA methylation significantly interacted with anxiety to moderate suicidal behavior that was not replicated in the GTP cohort. Although it is possible that our previously published anxiety results may be linked to underlying trauma exposure, this conclusion is not supported by the data. Instead, it is likely that the underlying factor resulting in significant interactions with SKA2 is differential HPA axis sensitivity, which is an underlying feature of both anxiety and trauma.

We identified a significant interaction between SKA2 variation and trauma at mediating the response to the DST, a metric of HPA axis sensitivity often dysregulated in suicidal individuals. Given the implicated role of SKA2 in facilitating glucocorticoid receptor nuclear transactivation and anticorrelated relationship with gene expression, the observed direction of association is consistent with our previously proposed interpretation that epigenetically driven decreases in SKA2 may inhibit the ability of glucocorticoid receptor to properly suppress natural stress response. This finding has relevance to other psychiatric disorders such as PTSD, which may have altered HPA axis sensitivity. The observed interaction is similar to that reported for other HPA axis relevant genes including CRHR1 and FKBP5. In both cases, high CTQ scores moderate the relationship between genetic variation and psychiatric symptoms or HPA-axis function. Indeed, FKBP5 has also been associated with depression, anxiety and PTSD. Such interactions with childhood maltreatment, including those observed for SKA2, may result from a differential priming of the HPA axis by early-life trauma. Similar to FKBP5, epigenetic alterations at SKA2 may adapt over time in the presence of heightened HPA axis sensitivity causing differential effects on the glucocorticoid receptor-negative feedback system dependent on the context of early-life exposure to stress and potentially mediated by the genetic and epigenetic context of relevant genes. These differential effects may predispose to stress-related disorders such as suicide and PTSD, which have been demonstrated to have opposing actions on the HPA axis, resulting in faster and slower clearing of post-stress cortisol, respectively. This interpretation is supported by the data as individuals with PTSD and no suicidal behaviors had generally lower CTQ scores compared with those with suicidal behavior. Thus, the observed interaction on HPA axis sensitivity may be a result of the differential contributions of these overlapping phenotypes in the subjects tested.

We observed that the SKA2 epigenetic and genetic biomarker predicted civilian PTSD cases when child abuse was incorporated. The degree to which our observations are based on comorbid phenotypes or substance use cannot be distinguished because of the observed significant association between trauma exposure, substance abuse, PTSD and suicidality. Further work will be necessary to distinguish the degree to which SKA2 is specific to suicide biology or more broadly affects other HPA axis-associated mental disorders such as PTSD. Future work in longitudinally collected samples will enable a robust way to test these hypotheses and to fully discern the cause versus effect nature of the identified associations of SKA2 with suicidal behaviors.

Supplementary Materials and Methods

Grady Trauma Project (GTP). The subjects for this study were part of a larger investigation of genetic and environmental factors that predict the response to stressful life events in a predominantly African American, urban population of low socioeconomic status.

Subjects were scored as having PTSD if they met DSM-IV criteria for lifetime PTSD based a structured interview (Clinician Administered PTSD Screen—CAPS—or the MINI International Neuropsychiatric Interview—M.I.N.I). Suicide attempt (SA) was measured as a binary response to the question: Have you ever tried to kill yourself or commit suicide? Current suicidal ideation (SI) was operationalized using item 9 of the Beck Depression Inventory (BDI), with SI being coded as present if the subject reports any of the following: 1) I have thoughts of harming myself but I would not carry them out, 2) I feel I would be better off dead, 3) I have definitive plans about committing suicide, 4) I feel my family would be better off if I were dead, or 5) I would kill myself if I could. Past history of substance abuse was captured by self-report in response the question: Have you ever had a problem with drug or alcohol abuse? The Childhood Trauma Questionnaire (CTQ) was used to assess physical, sexual, and emotional abuse during childhood based on the established scores for mild, moderate, and severe abuse for each type. All other lifetime trauma exposure was measured using the Traumatic Experiences Inventory (TEI). Finally, anxiety symptoms were assessed as a continuous score from the Hamilton Anxiety Scale (HAM-A).

All procedures were approved by the Institutional Review Board of Emory University School of Medicine and the Grady Health Systems Research Oversight Committee.

Johns Hopkins Center for Prevention Research Study (PRC). Data are from a prospective study conducted in the context of an epidemiologically-based group-randomized prevention trial. Details of the trial are available elsewhere.

All study metrics were derived as responses to a standardized interview. Attrition in the cohort was slightly greater among males and whites (p<0.01). Standardized assessments were conducted by trained non-clinical interviewers with the most recent wave collected via a computerized interview that was conducted by the interviewer, and when assessing potentially sensitive topics such as drug involvement, conducted by the respondent using the computer). A binary substance abuse metric was calculated such that individuals abusing or dependent on alcohol, tranquilizers, sedatives, marijuana, heroin, crack, cocaine, or other hallucinogens were coded as 1 and all those without reported abuse or dependence of any of these substances were coded as 0. Current suicidal ideation was determined at the interview closest to blood draw and measured as a binary response to the question: Have you ever felt so low you thought of committing suicide? Suicide attempt was measured as a binary response to the question: Have you ever attempted suicide? Childhood physical abuse that occurred prior to the age of 18 was assessed by self-report at 19-21 years of age. Subjects were asked "How often did your caregivers hit you hard enough to cause a bruise?" and "How often did your caregivers hit you hard enough to cause bleeding or break a bone?" Similarly, childhood emotional abuse was quantified by asking subjects "How often did your caregivers insult, swear, or yell at you?" and "How often did your caregivers threaten to end their relationships with you?" Responses were numerically quantified from 1 to 6 corresponding to "Never, Rarely", "Sometimes", "Often", "Most of the time", and "Always", respectively. Childhood sexual trauma was assessed by self-report on a section pf the 1996 Detroit Area Survey (Le-Niculescu et al., 164 MOL. PSYCHIATRY 118-112 (2013). Sexual abuse was coded as a binary variable for individuals who reported sexual assault or rape prior to the age of 18. A single childhood trauma score was derived by taking the Eigen vector of the first principle component of the responses across emotional, physical, and sexual abuse domains.

This study was approved by the Institutional Review Board at Johns Hopkins University. All participants provided informed consent to participate.

SKA2 Methylation Levels and Genotyping. SKA2 3'UTR DNA methylation levels at rs7208505 were determined using normalized beta values for the cg13989295 probe from the Illumina HumanMethylation450 BeadChip from data generated previously in the GTP cohort. Beta values were generated with BeadStudio and were set to missing (no call) if detection p-values exceeded 0.001. CpGassoc was used to remove samples with probe detection call rates <95% and those with an average intensity value of either <50% of the experiment-wide sample mean or <2,000 arbitrary units (AU). In addition, CpG sites with missing data for >10% of samples were excluded from analysis. Beta Mixture Quantile dilation (BMIQ) was used to normalize each dataset.

Figure 6A:
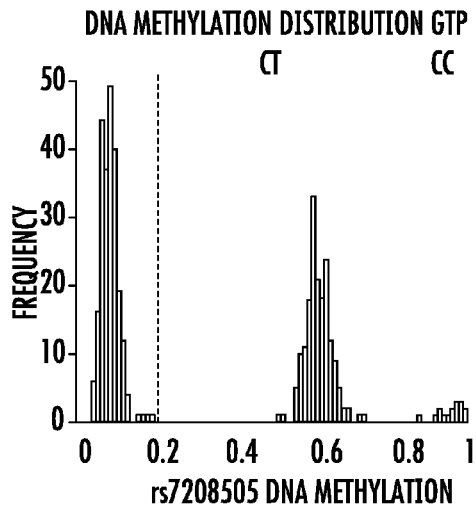
FIG. 6A-6B. Genotyping of rs7208505 from DNA methylation data.
Figure 6B:
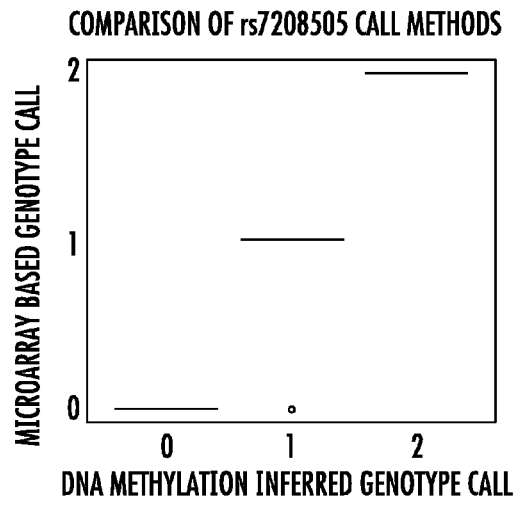

Genotyping was performed using the Omni-Quad 1M or the Omni Express BeadChip (Illumina). PLINK was used to perform quality control analyses such that SNPs that had a call rate <95%, a minor allele frequency (MAF) <0.05, or significant deviation from Hardy-Weinberg proportions (p<0.00001) were excluded, as were samples with >5% missing data. From this data, MaCH 1.0 was used to impute GTP genotypes for rs7208505 using unrelated individuals from HapMap ASW, CEU, LWK, MKK, TSI, and YRI Phase 3 reference samples. Out of 61 of 421 subjects were missing genotype calls. Based on the close correlation between SKA2 3'UTR DNA methylation and rs7208505, we inferred the genotype from the remaining 61 samples by the following method. We built a linear discriminant analysis of called genotypes as a function of DNA methylation at rs7208505. DNA methylation values for the 61 samples with missing genotypes were input into the model, generating genotype call predictions that were subsequently used. This method returned the exact same values as calling genotype based on which sub distribution of the trimodal methylation distribution the individual's methylation fell into (FIG. 6).

The genotype, suicide attempt, and associated beta value distribution per genotype are as follows: TT homozygotes, N=231, beta range=0.04-0.18, mean=0.083±0.021, suicide attempt N=53, non-attempt N=178; CT heterozygotes: N=174, beta range=0.49-0.69, mean=0.58±0.029 suicide attempt N=43, non-attempt N=31; CC homozygotes, N=16, beta range=0.82-0.92, mean=0.89±0.029, suicide attempt N=3, non-attempt N=12.

Effects of Certain Factors on Methylation. We assessed the effect that substance abuse, early life trauma and other potential confounding factors had on DNA methylation at rs7208505 using available information in the GTP cohort. After controlling for rs7208505 genotype, age, sex, only four factors demonstrated evidence for a significant effect on SKA2 DNA methylation including the first two principle components of ancestry based on previously published GWA data and past history of substance abuse (Table 4). Importantly, current substance abuse did not show a significant association (Table 4). Early life and adult trauma scores do not influence the levels of SKA2 DNA methylation directly (Table S2); however, a further analysis demonstrates that both childhood trauma question are (CTQ) totals and TEI scale derived adult trauma exposure totals are significantly associated with past substance abuse ($\beta=6.86\pm1.85$, $F=13.65$, $df=1/405$, $p=2.5\times10^{-4}$, and $\beta=2.29\pm0.3$, $F=57.01$, $df=1/402$, $p=2.9\times10^{-13}$, respectively). SKA2 DNA methylation demonstrated a continued association for post history of substance abuse when controlling for child abuse or lifetime trauma exposure as an additive covariate (Substance Abuse $\beta=-0.0063\pm0.0025$, $F=3.28$, $df=2/404$, $p=0.013$ and Substance Abuse $\beta=-0.0057\pm0.0027$, $F=2.3$, $df=2/401$, $p=0.034$ respectively). For this reason, in order to accurately assess model predictions with trauma independent of substance related decreases on SKA2 DNA methylation, we adjusted SKA2 DNA methylation levels for past history of substance abuse in all analyses where we could not include substance abuse as a covariate in the regression.

Supplementary Results

Figure 7:
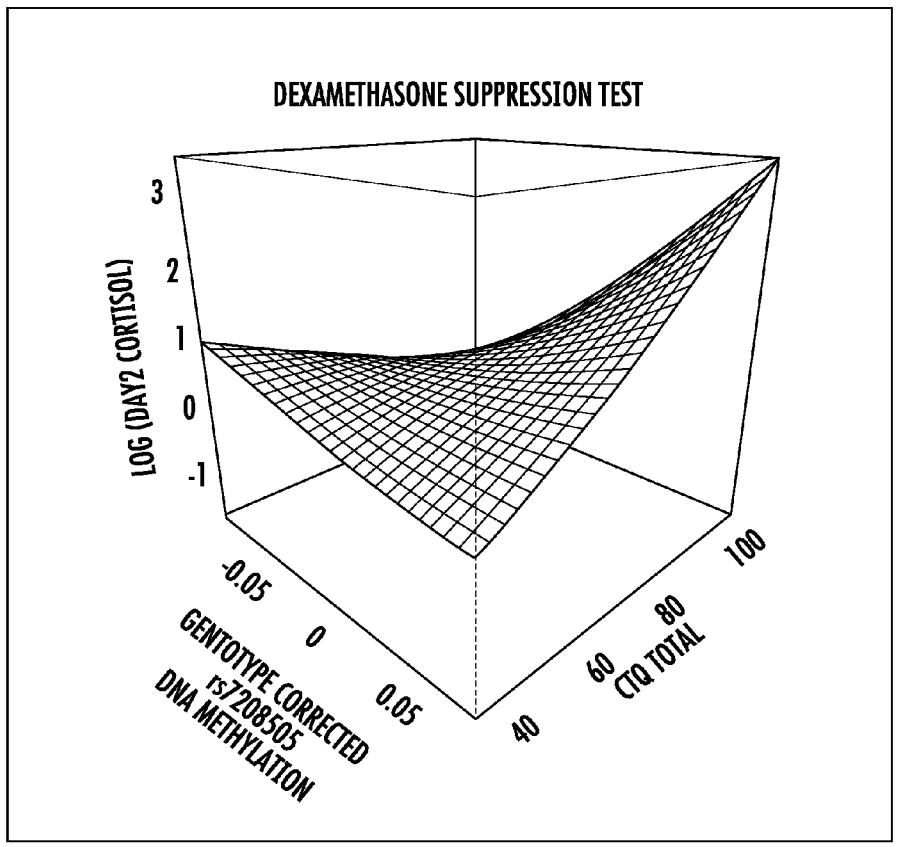
FIG. 7. SKA2 moderation of trauma on post DST cortisol levels. A three dimensional representation of the significant model of rs7208505 corrected SKA2 3'UTR DNA methylation (x axis) interacting with CTQ trauma scores (z axis) and its effect on the natural log of the day 2 cortisol values following the dexamethasone suppression test (y axis).
Figure 8A:
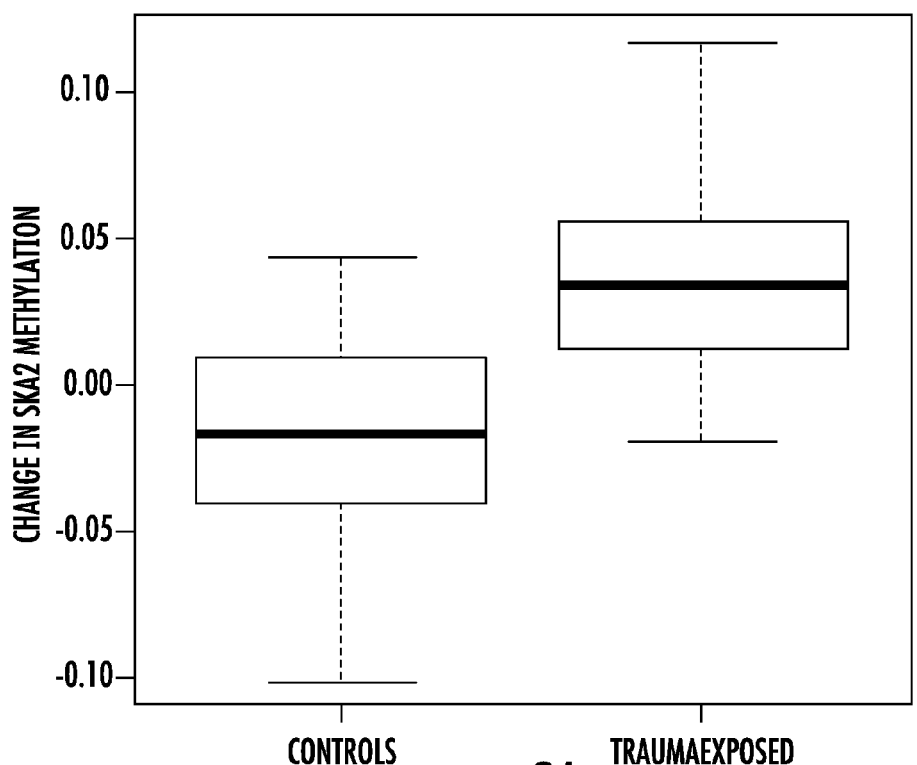
FIG. 8A-8B.
Figure 8B:
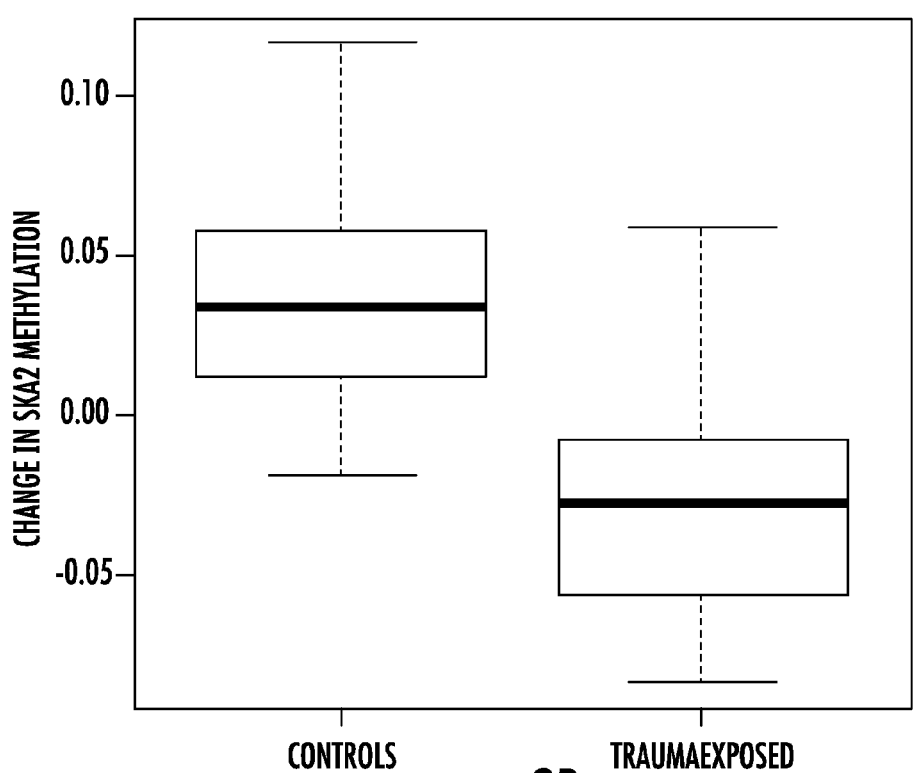

We performed the exploratory sliding window analysis on different subtypes of trauma reported in the CTQ including physical abuse, sexual abuse, and emotional abuse, assessing SKA2 3'UTR epigenetic and genetic prediction models on lifetime suicide attempt. The resulting plots demonstrate that emotional abuse most closely resembles the pattern observed for the total CTQ scores, while both physical and sexual abuse do not generate predictions for any windows where the 95% confidence limits do not include 0.5 (FIG. 7).

In the GTP cohort, the total anxiety score (HAM-A) is significantly associated with physical ($\beta=0.18\pm0.084$, $F=5.02$, $df=1/347$, $p=0.026$) and sexual ($\beta=0.38\pm0.11$, $F=12.94$, $df=1/348$, $p=3.7\times10^{-4}$) abuse but is most strongly associated with emotional abuse ($\beta=0.63\pm0.089$, $F=50.27$, $df=1/347$, $p=7.5\times10^{-12}$). The model performed significantly stronger in delineating 6 suicide attempters from 12 non-attempters experiencing severe emotional abuse but no to moderate physical or sexual abuse (AUC=0.81, 95% CI: 0.58-1, permuted p=0.066); however, the small sample size in this case resulted in only trend level significance and calls into question the usefulness of this refined prediction. Incorporation of CTQ emotional abuse scores as an interactive covariate improved model performance, generating a significant AUC of 0.86 (95% CI: 0.67-1, permuted p=0.028). This interactive model was also able to distinguish 5 PTSD cases from 9 non-PTSD cases who experienced severe emotional abuse but no to moderate physical or sexual trauma with an AUC of 0.84 (95% CI: 0.61-1, permuted p=0.066).

These findings should be interpreted in the context that there is often a higher prevalence of reported emotional relative to physical and sexual abuse in the population. The frequency of individuals categorized as experiencing severe physical and emotional abuse was similar at 26.6% and 25.6%, respectively, which is similar to the 24% reported by young adults in larger epidemiological surveys. The frequency of severe sexual abuse reported in the GTP was higher at 34.4%. These findings suggest the better performance of the emotional abuse metric in the model may not be driven by a larger portion of the cohort reporting this form of abuse and should be investigated further in future studies.

We assessed other CpGs within the SKA2 locus for association with either suicide or PTSD (Table 6). Many CpGs within the SKA2 gene were significantly correlated with rs7208505 genotype adjusted DNA methylation after Bonferroni correction (Table 6). No associations were observed with suicide attempt in a linear model correcting for age, sex, race, and past substance abuse. By contrast, three CpGs located in the SKA2 promoter region exhibited nominally significant association to PTSD that was not significant after correction for multiple testing. Gene expression decreases at SKA2 have been associated with suicidal behaviors and completed suicide. Our previous work identified a three way interaction between SKA2 3'UTR DNA methylation and that of microRNA 301a (miR-301a) (cg10822495) and three promoter CpGs proximal to a CREB1 binding site that drives SKA2 transcription in conjunction with miR-301a modulation ("cg01515809", "cg20009499", "cg17663700"). Similar to our previous study, we observed significant correlations between rs7208505 adjusted DNA methylation (cg13989295) and the CpGs in the miR-301a (Rho=0.23, $p=1.1\times10^{-6}$) and promoter region (Rho=−0.19, $p=9.8\times10^{-5}$). Peripheral blood gene expression levels for SKA2 derived from Illumina expression microarray probe (downloaded from http://www.ncbi.nlm.nih.gov/geo/Accession # GSE42002), ILMN_1807807, were not associated with suicide attempt or PTSD in this cohort (Wilcoxon Rank Sum Test Suicide: N=99, Mean=6.5+0.18, non-Suicide: N=321, Mean=6.5+0.17, p=0.29: PTSD: N=78, Mean=6.5+0.17, non-PTSD: N=203, Mean=6.5+0.17, p=0.79). We did observe a significant replication of the three-way interaction between SKA2 3'UTR, miR-301a, and CREB1 proximal CpG DNA methylation (Table 7). Similar results were obtained when using the average of all promoter CpGs (data not shown). Incorporation of the miR-301a and promoter CpGs into the interactive model with CTQ scores, correcting for age, sex, race, and past substance abuse improved the model R2 to 0.32 from 0.25 (Table 2, Table 7). No significant interactions were observed for this model with PTSD (data not shown); however, SKA2 promoter DNA methylation was independently associated with PTSD after controlling for CTQ, age, sex, race, and substance abuse history (b=7.67±3.6, F=7.9, df=8/261, p=0.034). Cumulatively, the data suggest that epigenetic variation in other gene expression relevant CpG regions of SKA2 may be important for modeling disease associated variation and should be investigated further in future studies.

TABLE 3

Clinical and Demographic Characteristics of the Cohorts

|  | GTP Blood, N = 421 | GTP Saliva, N = 61 | PRC Blood, N = 325 |
| --- | --- | --- | --- |
| Age, mean ± SD | 41.6 ± 12.7 | 42.4 ± 11.8 | 30.4 ± 2.5 |
| Female Sex, N (%) | 299 (71.0%) | 48 (78.7%) | 197 (60.6%) |
| African American Race, N (%) | 392 (93.1%) | 54 (88.5%) | 247 (76%) |
| SA Lifetime, N (%) | 99 (23.6%) | 19 (31.1%) | 48 (14.8%) |
| SI Current, N (%) | 67 (16.6%) | 8 (13.8%) | 78 (24%) |
| Current PTSD, N (%) | 78 (27.7%) | | |
| CTQ Total, mean ± SD | 43.7 ± 18.4 | 48.7 ± 23.4 | 131 (40.3%)* |
| Past Substance Abuse, N (%) | 151 (37.4%) | 24 (39.3%) | 96 (29.5%) |
| HAM-A Score, mean + SD | 11.1 ± 8.9 | 12.6 ± 9.7 | |

*Number (%) of individuals in the PRC cohort were classified as traumatized based on reported physical or sexual violence exposure.

TABLE 4

Confounding influences on SK42 DNA methylation

| Covariate | DNA methylation association with substance/diagnosis | | | | | Suicide association with substance/diagnosis | | | | |
|---|---|---|---|---|---|---|---|---|---|---|
| | β value | Error | F | DF | Model P | β value | Error | F | DF | Model P |
| Ancestry PC2 | 0.76 | 0.24 | 10 | 266 | 0.0016 | 8.2 | 4.1 | 4.1 | 266 | 0.044 |
| Ancestry PC1 | −0.25 | 0.096 | 6.6 | 266 | 0.011 | −2.3 | 1.6 | 2 | 266 | 0.15 |
| Lifetime Substance Abuse | −0.006 | 0.0025 | 5.6 | 413 | 0.019 | 0.27 | 0.041 | 42 | 413 | $2.5 \times 10^{-10}$ |
| Current Substance Abuse | −0.008 | 0.0053 | 2 | 409 | 0.16 | 0.12 | 0.091 | 1.7 | 409 | 0.19 |
| Lifetime Bipolar | −0.007 | 0.0061 | 1.5 | 357 | 0.23 | 0.27 | 0.1 | 7 | 356 | 0.0085 |
| Smoker Life | 0.001 | 0.0038 | 0.075 | 229 | 0.78 | 0.087 | 0.06 | 2.1 | 229 | 0.15 |
| Lifetime MDD | 0.0004 | 0.0026 | 0.027 | 354 | 0.87 | 0.15 | 0.043 | 12 | 353 | 0.0008 |
| Current MDD | 0.0005 | 0.0036 | 0.017 | 340 | 0.9 | 0.2 | 0.059 | 11 | 336 | 0.0009 |
| Current Bipolar | −1E−03 | 0.0084 | 0.013 | 357 | 0.91 | 0.0073 | 0.14 | 0.0028 | 356 | 0.96 |

TABLE 5

Trauma subtype interactive effects on suicide phenotypes

| Sample | PRC Suicidal Attempt (N = 325) | | |
|---|---|---|---|
| Model Terms | β value | Error | P value |
| DNAm | −0.01 | 0.0028 | 0.02 |
| C/T | 0.31 | 0.15 | 0.03 |
| C/C | 0.45 | 0.24 | 0.07 |
| Trauma | 0.04 | 0.03 | 0.21 |
| Age | −0.01 | 0.01 | 0.38 |
| Sex | 0.0027 | 0.04 | 0.95 |
| Past Substance Abuse | 0.15 | 0.04 | 0.0003 |
| DNAm × Emotional Abuse | 0.0036 | 0.0014 | 0.01 |
| C/T × Emotional Abuse | −0.14 | 0.07 | 0.05 |
| C/C × Emotional Abuse | −0.27 | 0.13 | 0.03 |
| F | 3 | | |
| DF | 12/257 | | |
| Model $R^2$ | 0.12 | | $5.91 \times 10^{-4}$ |
| DNAm | −0.0024 | 0.0025 | 0.33 |
| C/T | 0.23 | 0.13 | 0.09 |
| C/C | 0.37 | 0.25 | 0.14 |
| Trauma | 0.06 | 0.04 | 0.17 |
| Age | −0.01 | 0.01 | 0.44 |
| Sex | 0.01 | 0.05 | 0.83 |
| Past Substance Abuse | 0.15 | 0.041 | 0.0002 |
| DNAm × Physical Abuse | 0.0019 | 0.0019 | 0.32 |
| C/T × Physical Abuse | −0.15 | 0.10 | 0.13 |
| C/C × Physical Abuse | −0.34 | 0.20 | 0.09 |
| F | 2.49 | | |
| DF | 12/257 | | |
| Model $R^2$ | 0.1 | | 0.0043 |
| DNAm | 0.000 | 0.001 | 0.89 |
| C/T | 0.009 | 0.054 | 0.87 |
| C/C | 0.025 | 0.090 | 0.78 |
| Trauma | 0.28 | 0.082 | 0.001 |
| Age | −0.001 | 0.01 | 0.89 |
| Sex | 0.000 | 0.04 | 1.00 |
| Past Substance Abuse | 0.11 | 0.036 | 0.003 |
| DNAm × Sexual Abuse | 0.002 | 0.003 | 0.46 |
| C/T × Sexual Abuse | −0.03 | 0.15 | 0.84 |
| C/C × Sexual Abuse | −0.37 | 0.23 | 0.11 |
| F | 3.6 | | |
| DF | 12/257 | | |
| Model $R^2$ | 0.13 | | $2.66 \times 10^{-5}$ |

TABLE 6

Association of SKA2 CpG probes with suicide attempt (SA), PTSD, and SKA2 3'UTR methylation

| | Chr 17 | SA Association | | | PTSD Association | | | SKA2 3'UTR+ Association | |
|---|---|---|---|---|---|---|---|---|---|
| Probe ID | Position | β value | Error | P value | β value | Error | P value | Rho | P value* |
| cg01964121 | 54571258 | 9.11 | 12.55 | 0.47 | 18.06 | 15.48 | 0.24 | 0.20 | $6.01 \times 10^{-4}$ |
| cg10325038 | 54571266 | 0.03 | 0.63 | 0.96 | 1.25 | 0.79 | 0.11 | 0.20 | $5.82 \times 10^{-4}$ |
| cg10822495 | 54583355 | −0.02 | 0.54 | 0.97 | −0.09 | 0.72 | 0.90 | 0.26 | $1.94 \times 10^{-6}$ |
| cg02656609 | 54583400 | −0.48 | 1.37 | 0.73 | −2.27 | 1.93 | 0.24 | 0.22 | $8.72 \times 10^{-5}$ |
| cg07505964 | 54584296 | 0.05 | 1.01 | 0.96 | 0.30 | 1.46 | 0.84 | 0.24 | $1.68 \times 10^{-5}$ |
| cg19273756 | 54584473 | 0.04 | 0.71 | 0.95 | 0.38 | 1.00 | 0.71 | 0.16 | 0.02 |
| cg12169852 | 54586508 | 2.24 | 3.34 | 0.50 | 0.64 | 4.43 | 0.88 | −0.10 | 1 |
| cg07333037 | 54586638 | 1.37 | 2.47 | 0.58 | −5.08 | 3.33 | 0.13 | −0.17 | $6.95 \times 10^{-3}$ |
| cg09972077 | 54587073 | 0.80 | 1.56 | 0.61 | −1.62 | 2.08 | 0.44 | −0.16 | 0.01 |
| cg01515809 | 54587178 | 0.69 | 1.25 | 0.58 | −3.59 | 1.66 | 0.031 | −0.17 | 0.01 |
| cg20009499 | 54587349 | 1.02 | 4.66 | 0.83 | −1.47 | 6.33 | 0.82 | −0.15 | 0.04 |
| cg17663700 | 54587356 | −2.49 | 3.47 | 0.47 | −0.96 | 4.87 | 0.84 | −0.17 | 0.01 |
| cg17989037 | 54587366 | −9.31 | 11.19 | 0.41 | −31.82 | 16.02 | 0.048 | −0.13 | 0.19 |
| cg27512082 | 54587671 | −0.27 | 4.55 | 0.95 | −2.86 | 6.28 | 0.65 | −0.21 | $2.68 \times 10^{-4}$ |
| cg12941374 | 54587743 | 1.08 | 4.02 | 0.79 | −9.89 | 5.11 | 0.054 | −0.11 | 0.40 |
| cg16861410 | 54587795 | 0.14 | 5.39 | 0.98 | −0.63 | 8.34 | 0.94 | −0.16 | $1.77 \times 10^{-2}$ |

TABLE 6-continued

Association of SKA2 CpG probes with suicide attempt (SA), PTSD, and SKA2 3′UTR methylation

| Probe ID | Chr 17 Position | SA Association | | | PTSD Association | | | SKA2 3′UTR[+] Association | |
|---|---|---|---|---|---|---|---|---|---|
| | | β value | Error | P value | β value | Error | P value | Rho | P value* |
| cg02573089 | 54587824 | −1.23 | 2.98 | 0.68 | 1.57 | 3.97 | 0.69 | −0.07 | 1 |
| cg19178362 | 54587829 | −1.70 | 2.64 | 0.52 | 1.68 | 3.50 | 0.63 | −0.19 | $2.04 \times 10^{-3}$ |
| cg09726208 | 54587840 | 1.59 | 2.35 | 0.50 | −1.76 | 3.21 | 0.58 | −0.14 | 0.09 |
| cg11214846 | 54587848 | −0.42 | 2.71 | 0.88 | 0.37 | 3.73 | 0.92 | −0.12 | 0.32 |
| cg24616461 | 54587897 | −1.28 | 2.16 | 0.55 | −4.62 | 2.93 | 0.12 | −0.26 | $1.51 \times 10^{-6}$ |

*= Bonferroni corrected
[+]= methylation levels of cg13989295 adjusted for rs7208505 genotype

TABLE 7

Interaction of additional SKA2 CpGs

| Model Term | β value | Error | P value |
|---|---|---|---|
| | SKA2 Gene Expression | | |
| 3′UTR DNAm | −36.14 | 17.86 | 0.044 |
| miR-301a | 17.41 | 9.41 | 0.065 |
| Promoter | 30.36 | 14.74 | 0.040 |
| rs7208505 C/T | 7.99 | 4.46 | 0.074 |
| rs7208505 C/C | 412.16 | 249.66 | 0.100 |
| 3′UTR DNAm X miR-301a | 39.82 | 19.05 | 0.037 |
| rs7208505 C/T X miR-301a | −19.24 | 10.01 | 0.055 |
| rs7208505 C/C X miR-301a | −33.42 | 15.64 | 0.033 |
| 3′UTR DNAm X Promoter | 2114.15 | 1043.75 | 0.044 |
| rs7208505 C/T X Promoter | −1030.88 | 544.90 | 0.059 |
| rs7208505 C/C X Promoter | −1775.05 | 873.11 | 0.043 |
| miR-301a X Promoter | −456.64 | 267.24 | 0.088 |
| 3′UTR DNAm X miR-301a X Promoter | −2327.62 | 1120.33 | 0.039 |
| rs7208505 C/T X miR-301a X Promoter | 1137.94 | 583.74 | 0.052 |
| rs7208505 C/C X miR-301a X Promoter | 1951.51 | 933.69 | 0.037 |
| F | 0.98 | | |
| DF | 15/341 | | |
| Model $R^2$ | 0.4 | | 0.45 |
| | Suicide Attempt | | |
| 3′UTR DNAm | 186.80 | 112.10 | 0.10 |
| rs7208505 C/T | −94.71 | 57.07 | 0.10 |
| rs7208505 C/C | −95.25 | 106.80 | 0.37 |
| miR-301a | −45.87 | 28.14 | 0.10 |
| Promoter | −2565.00 | 1418.00 | 0.071 |
| CTQ | −0.89 | 0.65 | 0.17 |
| Age | 0.00 | 0.00 | 0.90 |
| Sex | 0.12 | 0.04 | 0.0039 |
| Race1 | 0.08 | 0.09 | 0.34 |
| Race2 | 0.63 | 0.24 | 0.010 |
| Race3 | 0.03 | 0.37 | 0.93 |
| Substance Abuse History | 0.16 | 0.05 | 0.0007 |
| 3′UTR DNAm X miR-301a | −217.00 | 120.90 | 0.074 |
| rs7208505 C/T X miR-301a | 110.00 | 61.51 | 0.075 |
| rs7208505 C/C X miR-301a | 116.50 | 114.20 | 0.31 |
| 3′UTR DNAm X Promoter | −12660.00 | 6052.00 | 0.037 |
| rs7208505 C/T X Promoter | 6155.00 | 3081.00 | 0.047 |
| rs7208505 C/C X Promoter | 8633.00 | 6116.00 | 0.16 |
| miR-301a X Promoter | 2928.00 | 1529.00 | 0.056 |
| 3′UTR DNAm X CTQ | −4.12 | 2.80 | 0.14 |
| rs7208505 C/T X CTQ | 2.08 | 1.39 | 0.13 |
| rs7208505 C/C X CTQ | 1.46 | 3.00 | 0.63 |
| miR-301a X CTQ | 1.05 | 0.69 | 0.13 |
| Promoter X CTQ | 63.37 | 33.41 | 0.059 |
| 3′UTR DNAm X miR-301a X Promoter | 14330.00 | 6529.00 | 0.029 |
| rs7208505 C/T X miR-301a X Promoter | −6991.00 | 3325.00 | 0.036 |
| rs7208505 C/C X miR-301a X Promoter | −9880.00 | 6549.00 | 0.13 |
| 3′UTR DNAm X miR-301a X CTQ | 4.80 | 2.99 | 0.11 |
| rs7208505 C/T X miR-301a X CTQ | −2.43 | 1.48 | 0.10 |
| rs7208505 C/C X miR-301a X CTQ | −1.90 | 3.19 | 0.55 |
| 3′UTR DNAm X Promoter X CTQ | 301.60 | 144.40 | 0.037 |
| rs7208505 C/T X Promoter X CTQ | −145.70 | 72.06 | 0.044 |
| rs7208505 C/C X Promoter X CTQ | −180.60 | 173.40 | 0.30 |

TABLE 7-continued

Interaction of additional SKA2 CpGs

| Model Term | β value | Error | P value |
|---|---|---|---|
| miR-301a X Promoter X CTQ | −71.47 | 35.79 | 0.047 |
| 3'UTR DNAm X miR-301a X Promoter X CTQ | −338.10 | 154.80 | 0.030 |
| rs7208505 C/T X miR-301a X Promoter X CTQ | 164.10 | 77.34 | 0.035 |
| rs7208505 C/C X miR-301a X Promoter X CTQ | 206.10 | 184.70 | 0.27 |
| F | | 4.68 | |
| DF | | 37/369 | |
| Model R$^2$ | | 31.94 | 2.8 × 10$^{-15}$ |

Example 3

SKA2 Methylation is Involved in Cortisol Stress Reactivity and Predicts the Development of Post-Traumatic Stress Disorder (PTSD) After Military Deployment Genomic variation in the SKA2 gene has recently been identified as a promising suicide biomarker. In light of its role in glucocorticoid receptor transactivation, we investigated whether SKA2 DNA methylation influences cortisol stress reactivity and is involved in the development of post-traumatic stress disorder (PTSD). Increased SKA2 methylation was significantly associated with lower cortisol stress reactivity in 85 healthy individuals exposed to the Trier Social Stress Test (B=−173.40, t=−2.324, p=0.023). Next, we observed that longitudinal decreases in SKA2 methylation after deployment were associated with the emergence of post-deployment PTSD symptoms in a Dutch military cohort (N=93) (B=−0.054, t=−3.706, p=3.66×10−4). In contrast, exposure to traumatic stress during deployment by itself resulted in longitudinal increases in SKA2 methylation (B=0.037, t=4.173, p=6.98×10−5). Using pre-deployment SKA2 methylation levels and childhood trauma exposure, we found that the previously published suicide prediction rule significantly predicted post-deployment PTSD symptoms (AUC=0.66, 95% CI: 0.53-0.79) with an optimal sensitivity of 0.81 and specificity of 0.91. Permutation analysis using random methylation loci supported these findings. Together, these data establish the importance of SKA2 for cortisol stress responsivity and the development of PTSD and provide further evidence that SKA2 is a promising biomarker for stress-related disorders including PTSD.

Introduction

Prevalence rates of posttraumatic stress disorder (PTSD) in military personnel following deployment range from 5 to 15% (Sundin et al. 2010; Reijnen et al. 2015). Even though several risk factors for deployment-related PTSD have been identified (Sandweiss et al. 2011), the etiology of PTSD is currently not fully understood. It is therefore not possible to accurately identify who is at risk for PTSD after exposure to traumatic stress, and no reliable blood-based biomarkers for PTSD vulnerability have been identified so far. Nevertheless, prediction of deployment-related PTSD vulnerability is of great importance as it would facilitate prevention of the detrimental social and personal consequences of PTSD. Recent studies have shown that epigenetic mechanisms are important for successful adaptation to a stressful environment and play a role in the development of PTSD (Zovkic et al. 2013). DNA methylation is an important epigenetic mechanism that is influenced by genetic and environmental factors (Malan-Muller et al. 2014), and reflects the transcriptional status of a particular gene (Schubeler 2015). DNA methylation studies therefore have great potential to increase our understanding of how the interaction between an individual's genetic background and traumatic stress exposure results in the development of PTSD (Vinkers et al 2015). Kaminsky and colleagues recently proposed the spindle and kinetochore associated protein 2 (SKA2) gene (Chr17:59110368) as a blood-based DNA methylation biomarker for suicide (Guintivano et al. 2014). In their study, SKA2 methylation levels predicted suicide and were also related to lower levels of the stress hormone cortisol, consistent with a role in glucocorticoid receptor transactivation (Rice et al. 2008). Since PTSD is associated with enhanced GR sensitivity and lower physiological hypothalamic-pituitary-adrenal (HPA) axis activity (Mehta and Binder 2012; de Kloet et al. 2006; Yehuda et al. 1991) as well as with higher suicide rates (Schoenbaum et al. 2014), these findings raise the question whether the epigenetic SKA2 biomarker can also be of use for detecting who is at risk for PTSD. We hypothesize that changes in SKA2 methylation are dissimilar between PTSD-susceptible individuals and those who are resilient.

To investigate the involvement of SKA2 methylation, we used data from two independent cohorts. First, in order to understand how SKA2 methylation levels are related to the endocrine adaptation to stress, we examined the relationship between SKA2 methylation and the cortisol stress response in healthy individuals. Second, we prospectively investigated changes in SKA2 methylation in relation to the development of PTSD symptoms using data from a longitudinal Dutch military cohort (Boks et al. 2015) in which blood-based DNA methylation levels of SKA2 were measured before and 6 months after deployment to Afghanistan. Third, we investigated whether the epigenetic SKA2 biomarker rule developed for suicide (Guintivano et al. 2014) is capable of predicting PTSD before deployment.

Materials and Methods

Figure 10:
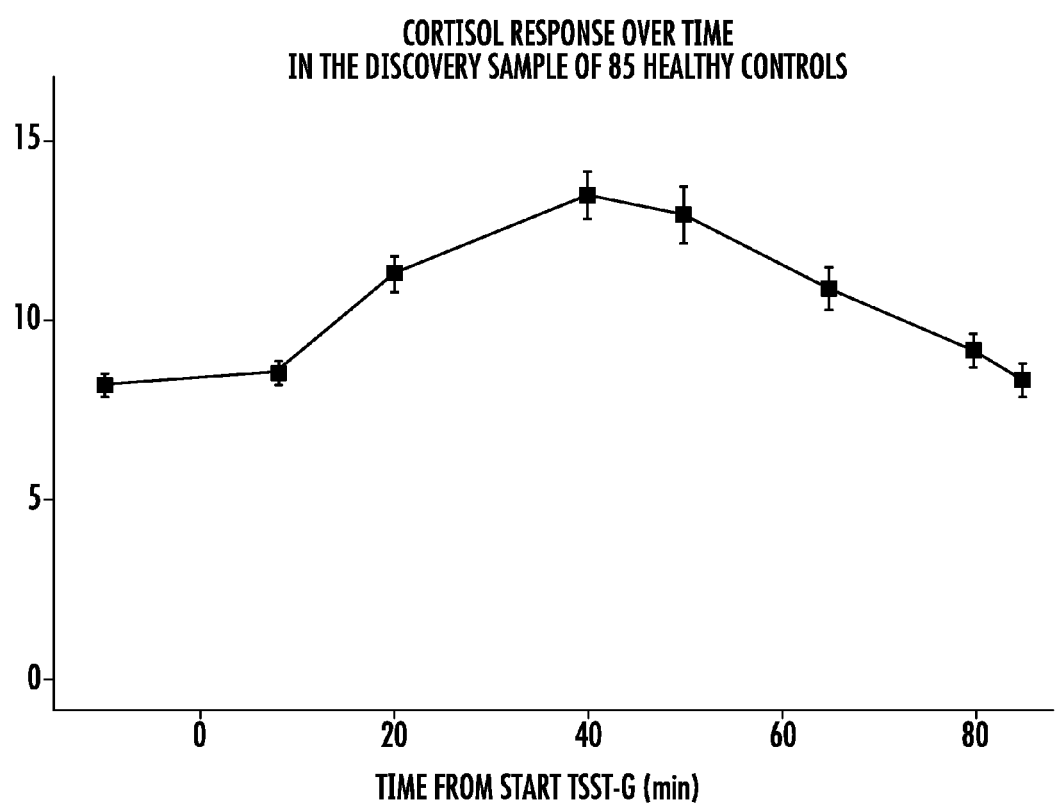
FIG. 10. Cortisol response to the Trier Social Stress Test.

Cortisol stress sample. Eighty-five healthy individuals were recruited from the general population at the University Medical Center, Utrecht, The Netherlands. Participants had three or more Dutch grandparents and had not been enrolled in stress-related research before (Vinkers et al. 2013; Houtepen et al. 2015) (Table 8). The absence of any mental or physical disorder was confirmed by an independent rater. Participants did not take heavy meals, drinks other than water or carry out heavy exercise at least 2 hours before the study protocol. Current use of psychoactive substances (amphetamines, MDMA, barbiturates, cannabinoids, benzodiazepines, cocaine, and opiates) was determined by self-report and verified with a urine multi-drug screening device (InstantView). Participants completed a group version of the Trier Social Stress Test (G-TSST), consisting of a public speaking test and an arithmetic task as previously published (Houtepen et al. 2015). Cortisol stress reactivity was assessed using eight saliva samples (Salivettes) collected over a time period of 90 minutes (FIG. 10). Samples were directly stored at −80° C. and analyzed as previously described (Houtepen et al. 2013). In short, cortisol was measured without extraction using an in house competitive radio-immunoassay. The area under the curve increase (AUCi) of cortisol was calculated based on the consecutive data points as described by Pruessner et al (2003).

TABLE 8

Characteristics of the cortisol stress reactivity sample (N = 85)

| Characteristics | (N = 85) |
|---|---|
| Sex (% female) | 50.5% |
| Mean age (sd) | 33 (15.84) |
| Race (% European Caucasian) | 100% |
| Childhood trauma (mean and sd) | 31.9 (8.2) |
| Cortisol stress reactivity (mean AUCi, sd) | 242.3 (419.64) |

Childhood trauma was assessed using the 25-item of the Childhood Trauma Questionnaire (CTQ) (Bernstein et al. 2003). The validity of the CTQ, including a Dutch translation, has been demonstrated in clinical and community samples (Bernstein et al. 2003; Thombs et al. 2009). One translated item (I believe I was molested) was excluded as this translation was found to be an invalid indicator of childhood sexual abuse in a previous validation study (Thombs et al. 2009).

Figure 13:
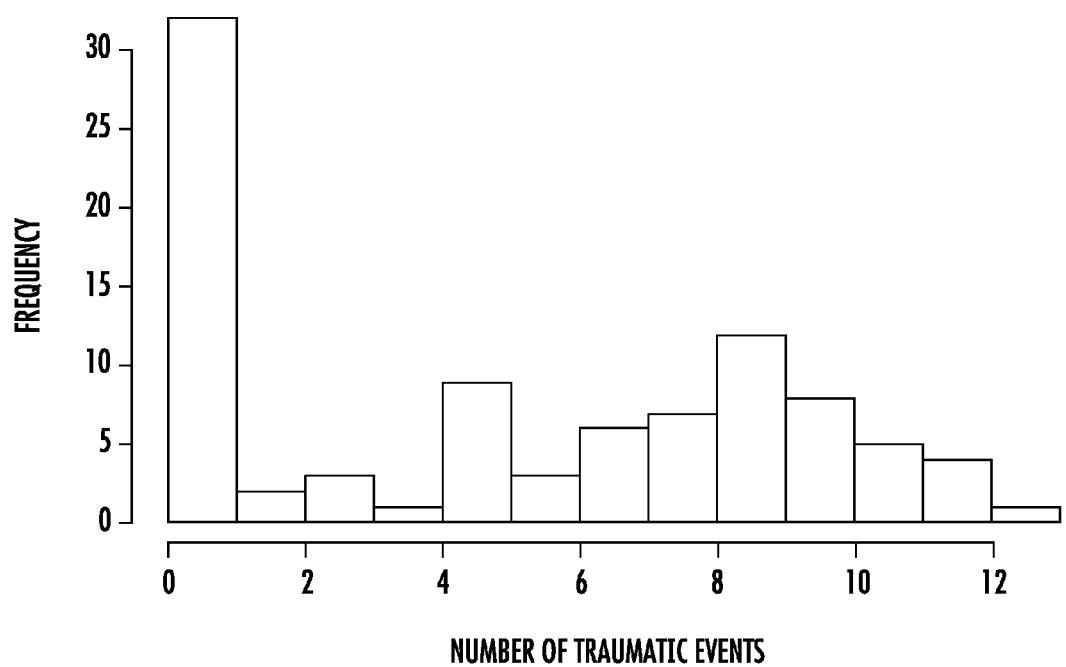
FIG. 13. Histogram of trauma distribution.

Military sample. From a large prospective cohort of 1032 Dutch military personnel deployed to Afghanistan (Van Zuiden et al. 2011), three approximately equally sized male subgroups (total N=94) were selected based on level of traumatic stress exposure and presence of PTSD symptoms (Table 9). In this selected sample we analyzed the association of longitudinal changes of SKA2 methylation with trauma exposure and PTSD symptom increase. Sample size was determined based on previous studies of cortisol response in healthy controls (cortisol stress sample). Blood samples were collected before and 6 months after deployment. Current PTSD symptoms over the past 4 weeks were assessed with the 22-item Self-Report Inventory for PTSD (SRIP) which has a good reliability and validity compared to other PTSD scales such as the Clinical Administered PTSD scale and the Mississippi scale for PTSD (Keane et al. 1988; Hovens et al. 2000). Development of PTSD was defined as a score of 38 and higher at follow-up in agreement with our previous studies (Van Zuiden et al. 2011). Exposure to combat trauma during deployment was assessed with a 19-item deployment experiences checklist (DEC) as previously published (Reijnen et al. 2015). This self-report assessment provided a range of potentially traumatic experiences that occur as part of deployment which include direct combat stressors. Trauma exposure was defined as more than 1 traumatic event. This pre-set dichotomization is based on the selection of participants with low or high levels of trauma in order to increase power (Boks et. al. 2007) and leads to a bivariate distribution of trauma levels (see FIG. 13 for histogram).

After exclusion of one outlier (see below) 93 participants were analyzed: i) N=32 with high combat trauma exposure (DEC, mean=7.3, SD=2.9) and high levels of postdeployment PTSD symptoms (SRIP, mean=45.3, SD=8.6), ii) N=29 with high combat trauma exposure (DEC mean=8.6, SD=2.3) and low levels of PTSD symptoms (SRIP=26.0 sd=3.7), and iii) N=32 with low combat trauma exposure (DEC mean=0.4, SD=0.5) and low levels of post-deployment PTSD symptoms (SRIP mean=25.1, sd=3.7) (Table 9). Analysis of age, gender, alcohol consumption, cigarette smoking, military rank, length, weight, or medication use did not show any differences between these three groups. Childhood trauma was assessed with the 27-item Dutch version of the Early Trauma Inventory-self report (ETI-SR) (Bremner et al. 2007), assessing early traumatic experiences before the age of 18 years which include general trauma, physical abuse, emotional abuse and sexual abuse (Hovens et al. 2000; Witteveen et al. 2006; Hovens et al. 2002; Witteveen et al. 2006). In order to investigate the specificity of changes in PTSD symptoms we also investigated SCL-90 total score (psychoneuroticism) as well as the depression, somatisation, agoraphobia and anxiety sub scales (Derogatis et al. 1973). Differences in PTSD symptoms between time points were log-transformed in order to improve the distribution. Three missing values in the baseline measure of PTSD symptoms were replaced by median values. This study was approved by the Medical Ethics Committee of the University Medical Center Utrecht and conducted in accordance with the Declaration of Helsinki and all participants gave written informed consent.

TABLE 9

Demographic and clinical characteristics of the military sample

| Characteristics | All (N = 93) | PTSD (N = 32) | High trauma (N = 29) | Low trauma (N = 32) |
|---|---|---|---|---|
| Post-deployment PTSD symptoms | | High | Low | Low |
| Traumatic stress | | High | High | Low |
| Race (% European Caucasian) | 100% | 100% | 100% | 100% |
| Age (SD) | 27.5 (9.1) | 26.8 (9.6) | 27.7 (9.1) | 28.1 (8.8) |
| Mean Trauma score (SD) | 5.3 (4.2) | 7.3 (2.9) | 8.6 (2.3) | 0.4 (0.5) |
| PTSD pre-deployment | 26.4 (3.9) | 27.9 (4.1) | 26.0 (3.8) | 25.4 (3.4) |
| PTSD symptoms at follow up (SD) | 32.4 (11.1) | 45.3 (8.6) | 26.0 (3.7) | 25.1 (3.7) |
| Change PTSD symptoms (SD) | 5.9 (10.8) | 17.4 (10.1) | 0.0 (3.6) | −0.3 (4.8) |
| Change in SCL-90 | 6.6 (21.8) | 20.4 (31.0) | 0.8 (11.5) | 0.7 (10.1) |
| Childhood trauma | 3.1 (2.7) | 4.8 (3.1) | 3.2 (2.3) | 1.3 (1.1) |
| Number of Deployment | 0.9 (1.2) | 0.8 (1.2) | 1.2 (1.5) | 0.6 (0.8) |
| Time to follow-up (months) (SD) | 13.5 (3.7) | 13.4 (3.8) | 13.5 (3.2) | 13.4 (3.7) |

Figure 11:
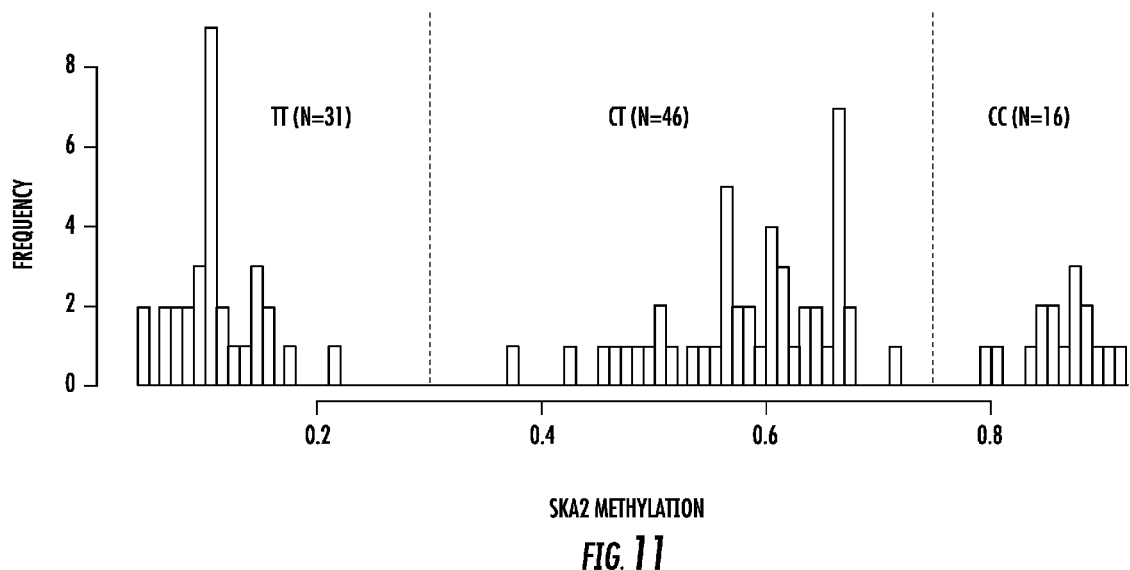
FIG. 11. Genotype inference SKA2.

SKA2 genotype and methylation. In both the stress reactivity and the military sample, whole blood EDTA samples were obtained and DNA was extracted using standard salting procedures. DNA concentration was assessed using riboGreen and integrity using BioAnalyser. Bisulphite conversion was conducted using Zymo kits under standard protocol. In both samples, DNA methylation levels were assessed using Illumina 450K DNA methylation arrays interrogating over 450,000 CpG loci per sample at single-nucleotide resolution and covering 99% of RefSeq genes and 96% of CpG islands. For the military sample, baseline and follow up samples were positioned on the same array and exposure to trauma and PTSD outcomes were equally distributed over the 16 arrays to reduce any batch effects to the minimum. For all analyses, SKA2 methylation levels (cg13989295) were adjusted for age and genotype of the underlying SNP (rs7208505) using inference of genotype based on the distributions of methylation levels as previously employed (Guintivano et al. 2014). Analyses of our data showed that SKA2 genotypes completely separate methylation distributions (FIG. 11). Adjusted SKA2 methylation levels were derived by taking the residuals of a linear model with age and genotype as indicator. One outlier of SKA2 methylation levels, defined as more than three standard deviations from the mean, was excluded from analyses.

Figure 12:
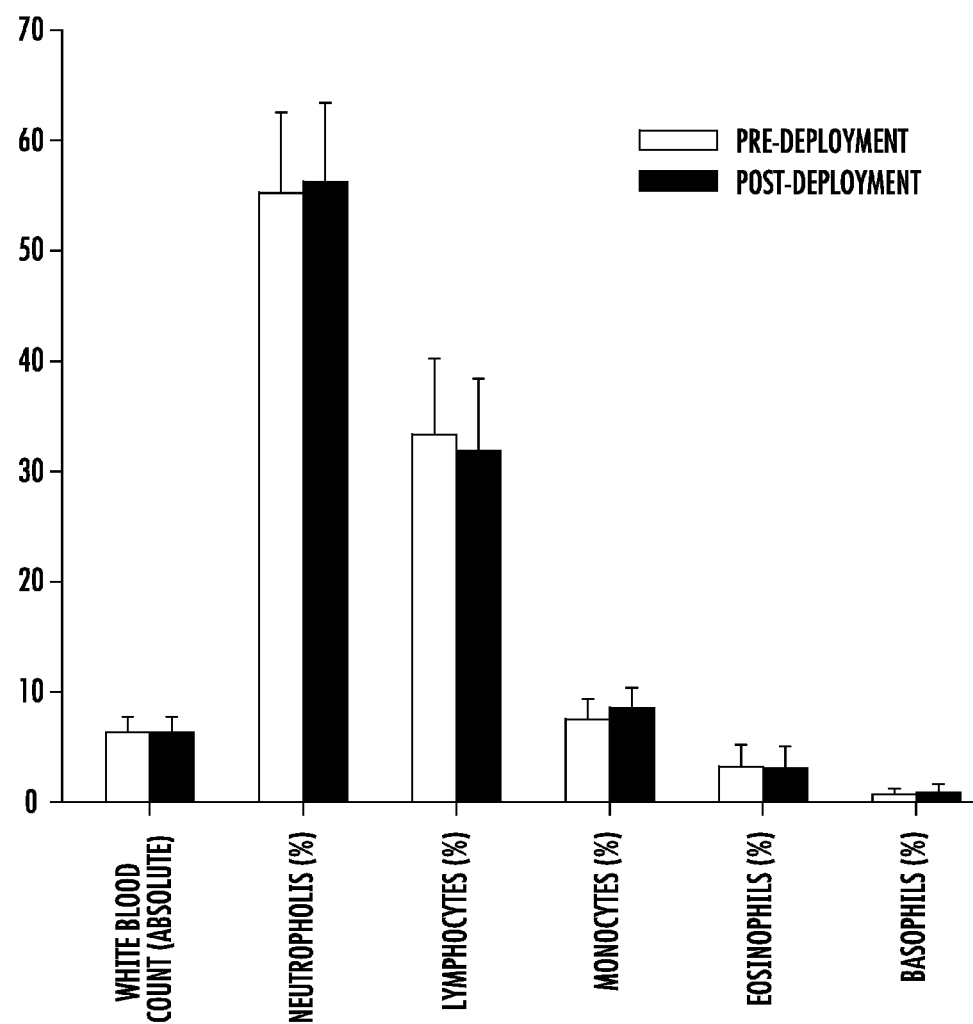
FIG. 12. Cell type composition before and after deployment. No significant differences were found between cell counts.

Cell type composition. Cell type composition was assessed in light of its potential influence on DNA methylation. In the military sample, cell type composition was investigated using flow cytometry analysis as implemented in the clinical laboratory of our University Medical Center as previously published (Van Zuiden et al. 2009) (FIG. 12). In the cortisol stress sample, cell-count estimation was calculated based on a recent algorithm (Jaffe and Irizarry 2014). The effect of cell count composition on SKA2 methylation levels was analyzed for both samples.

Statistical analysis. In the cortisol stress sample, linear regression was carried out with SKA2 methylation as the main determinant of the stress-induced cortisol area under the curve (AUCi), age and gender and childhood trauma as covariates (cortisol_AUCi~SKA2 methylation+age+gender+childhood trauma). Mediation analysis was conducted using the mediate package in R that implements a bootstrapping procedure to infer if changes in SKA2 methylation that are accounted for by childhood trauma can explain the association of childhood trauma with cortisol response. This effectively estimates the extent to which SKA2 methylation levels explain the association between childhood trauma and the cortisol stress response.

In the military sample, longitudinal analysis were conducted with SKA2 methylation after deployment as the outcome using linear regression with baseline SKA2 methylation levels as a covariate. First, we analyzed all participants together in a model with indicators of trauma and PTSD simultaneously (SKA2 methylation post-deployment ~SKA2 methylation pre-deployment+change in PTSD symptoms+trauma exposure). Next, to further separate effects of trauma and PTSD on SKA2 methylation, stratified analyses were carried out after exclusion of either participants who were not exposed to trauma (investigating PTSD symptoms in the trauma-exposed group) and excluding those individuals who developed post-deployment PTSD symptoms (investigating trauma effects in the non-PTSD group). All models were analyzed, with and without childhood trauma and the interaction term of childhood trauma and traumatic stress. Permutations with 100,000 random CpG methylation levels were used to derive an empirical p-value and estimate of the degree to which the association with traumatic stress and PTSD is unique or is an artifact of the underlying data structure. To investigate the effect of time we used a paired t-test to compare pre- and post-deployment SKA2 methylation levels.

To validate the previously published SKA2 suicide prediction rule (Guintivano et al. 2014) for its utility to predict PTSD, we used the model from the published training set in suicide victims on our data with the same published model parameters. The prediction rule was analyzed for predictive performance using a model with PTSD as dependent and SKA2 methylation and genotype in interaction with premorbid stress (suicide ~(SKA2 methylation+genotype)*childhood trauma). P-values for prediction were obtained using $1 \times 10^5$ label swapping permutations. This model was further validated using permutation analyses comparing the performance of an adjusted SKA2 model from the training set (using genotype and age-adjusted SKA2 methylation levels) with $1 \times 10^5$ random CpGs from the 450K methylation array to derive an empirical p-value. In addition we created a new prediction rule for the prospective development of PTSD symptoms, which was investigated using ROC analyses with pre-deployment SKA2 methylation levels as indicators.

Assumptions of linear regression were evaluated by inspecting residuals. Cell type composition before and after deployment was compared using repeated measures analysis of variance. Potential confounding by cell-type was ruled out by analyzing the association between cell counts (Monocytes, CD8T cells, CD4T cells, B-cell and Natural Killer cells) with SKA2 methylation levels. In the cortisol stress sample, medication users and smokers were excluded. In the military sample, the potential influence of childhood trauma was investigated by adding continuous childhood trauma scores to the above mentioned models and by analyzing baseline differences between the PTSD and trauma groups using a one way ANOVA. The potential influence of cigarette smoking, alcohol use and medication was investigated by excluding participants with documented change in these parameters from the analysis (N=35, N=8 and N=18 respectively).

Results

SKA2 methylation is involved in cortisol stress reactivity. In 85 healthy individuals, a lower cortisol stress response was significantly associated with SKA2 methylation in a model including age, gender and childhood trauma (Table 10) (model fit: $F(4,84)=9.12$, $p<0.001$, $R^2=0.27$). Mediation analysis showed no evidence for a causal role of SKA2 methylation in the relationship between childhood trauma and cortisol reactivity (estimated proportion mediation=0.041%, 95% CI: −0.18-0.233, p=0.52).

Longitudinal changes in SKA2 methylation and the association with trauma and PTSD. In the military cohort, we investigated the relationship between traumatic stress during deployment, longitudinal changes in SKA2 methylation and PTSD symptoms. Concurrent analysis of trauma and PTSD showed that SKA2 methylation changes were negatively associated with the development of PTSD symptoms (B=−0.054, t=−3.706, p=3.66×10−4, empirical p-value=1.37× 10−3) and that trauma exposure during deployment was positively associated with change in SKA2 methylation (B=0.037, t=4.173, p=7.0×10−5, empirical p-value=6.4× 10−4). Addition of childhood trauma as covariate retained a significant association of SKA2 methylation with PTSD symptoms (B=−0.058, t=−3.880 p=2.0×10−4) and deployment-related traumatic stress (B=0.032, t=3.339, p=0.001235). Childhood trauma was not significantly associated with prospective changes in SKA2 methylation (B=0.002, t=1.291, p=0.20) nor did childhood trauma alter the effects of traumatic stress on SKA2 methylation (B=−0.001993, t=−0.325, p=0.75). Childhood trauma levels were not significantly different between the three groups (ANOVA $F(1,91)=0.079$, $p=0.78$). Also, no effect of time was present for SKA2 methylation (paired t-test, $t=-0.944$, $df=92$, p-value=0.348).

TABLE 10

Association of SKA2 methylation with cortisol response in healthy controls

|  | B | SE | t | P. value |
|---|---|---|---|---|
| SKA2 methylation | −173.404 | 74.624 | −2.324 | 0.02256 |
| Childhood trauma | −21.433 | 6.619 | −3.238 | 0.00172 |
| Age | 3.955 | 2.529 | 1.564 | 0.12164 |
| Gender | −254.208 | 78.359 | −3.244 | 0.00169 |

To examine the effects of traumatic stress and PTSD per se, we also conducted longitudinal stratified analyses in non-PTSD participants and trauma-exposed individuals, separately. Exposure to traumatic stress during deployment was associated with an increase in SKA2 methylation in individuals that did not develop PTSD symptoms after deployment ($B=0.005$, $t=4.195$, $p=9.47\times10-5$. Moreover, decreases in SKA2 methylation was associated with the development of deployment-related PTSD symptoms in individuals exposed to traumatic stress (excluding the participants that had low trauma exposures) ($B=-0.070$, $t=-4.298$, $p=6.7\times10-5$).

Tables 11 and 12 show the full models of the association of SKA2 methylation levels with traumatic stress exposure and PTSD symptoms for the combined as well as the stratified analysis. Exclusion of participants for who alcohol, smoking or medication use changed during deployment retained the association of PTSD symptoms with longitudinal changes in SKA2 methylation for medication use ($B=-0.060$, $t=-2.803$, $p=0.008$), smoking ($B=-0.069$, $t=-4.182$ $p=1.1\times10-4$), and alcohol use ($B=-0.075$ $t=-4.886$, $p=1.0\times10-5$).

TABLE 11

Association of SKA2 methylation with traumatic stress and PTSD in a combined analysis.

|  | B | SE | t | P. value |
|---|---|---|---|---|
| Baseline SKA2 methylation | 0.469469 | 0.068746 | 6.829 | 1.01e−09 |
| Change in PTSD symptoms | −0.054492 | −0.014705 | −3.706 | 3.66e−04 |
| Trauma exposure | 0.037289 | 0.008936 | 4.173 | 6.98e−05 |

Model fit: $F (89, 3) = 20.58$, $p = 3.24 \times 10-10$, Adjusted R squared: 0.39

TABLE 12

Association of SKA2 methylation with traumatic stress and PTSD in the stratified analyses.
Association of traumatic stress with SKA2 methylation at follow up in the non PTSD participants

|  | B | SE | t | P. value |
|---|---|---|---|---|
| Baseline SKA2 methylation | 0.509 | 0.082 | 6.243 | 5.41e−08 |
| Trauma exposure | 0.005 | 0.001 | 4.195 | 9.47e−05 |

Model fit: $F (2, 58) = 25.4$, $p < 0.001$, $R2 = 0.45$
Association of PTSD with SKA2 methylation at follow up in trauma exposed participants TABLE 12-continued

|  | B | SE | t | P. value |
|---|---|---|---|---|
| Baseline SKA2 methylation | 0.520 | 0.077 | 6.793 | 6.52e−09 |
| Change in PTSD symptoms | −0.070 | 0.016 | −4.298 | 6.66e−05 |

Model fit: $F (2, 58) = 26.3$, $p < 0.001$, $R2 = 0.46$

Increases in PTSD symptoms were positively correlated with increases of psychoneuroticism symptoms (SCL-90 total score, $r=0.5$, $p<0.001$). As a result, increases in psychoneuroticism in individuals exposed to traumatic stress were also significantly associated with longitudinal changes in SKA2 methylation ($B=-0.063$, $t=-2.073$, $p=0.043$, (model fit: $F(2,55)=16.6$, $p<0.001$, $R2=0.35$). In contrast, SKA2 methylation changes were not significantly associated with any of the SCL-90 subscales of depression, somatization, agoraphobia and anxiety (data not shown).

Figure 9:
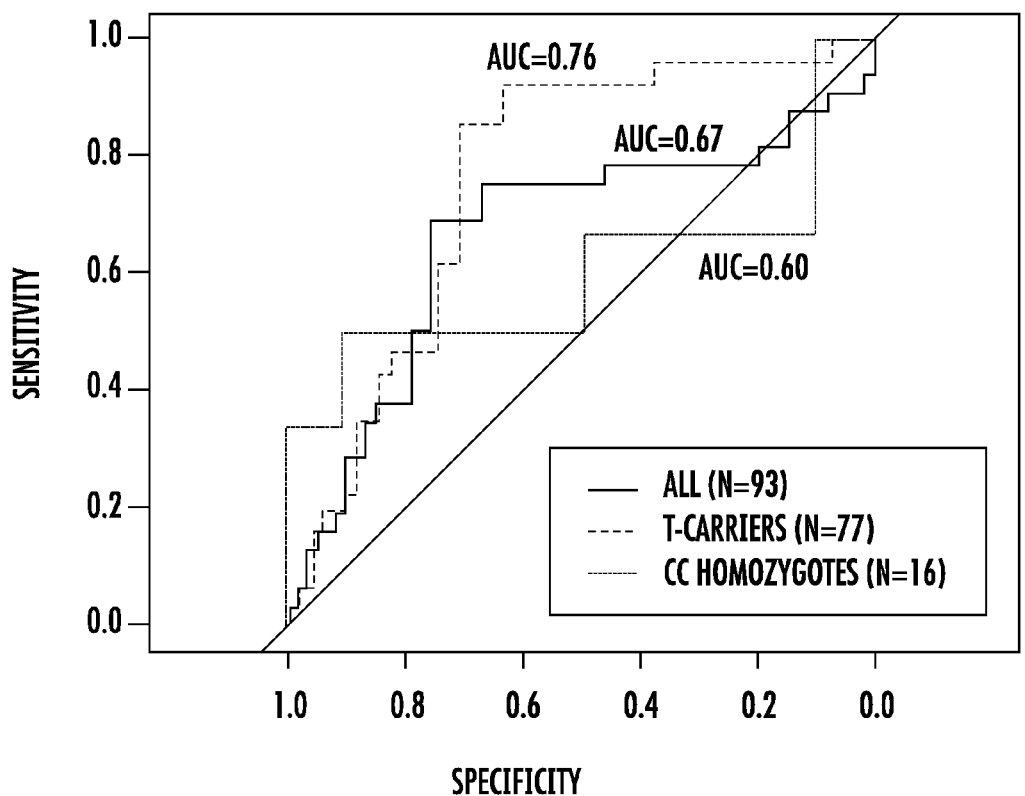
FIG. 9. PTSD prediction using pre-deployment SKA2 methylation based on the previously published SKA2 prediction rule (Guintivano et al. 2014).

PTSD prediction from SKA2. Finally, we investigated the prediction of PTSD symptoms from the previously published SKA2 suicide predictor rule (Guintivano et al. 2014). We found that the suicide prediction model provided modest but statistically significant prediction of PTSD from pre-deployment SKA2 methylation in a model including childhood trauma (AUC=0.66, 95% CI: 0.53-0.79, $p=0.011$). Optimal sensitivity was 0.81 with a specificity of 0.90. Permutation analysis showed that SKA2 methylation was a significantly stronger predictor than random CpGs (permuted p value=1.5e-4). Subsequent stratified prediction analyses were carried out to identify the genotypes for which prediction was optimal, since SKA2 methylation is in part under genetic control. In T-allele carriers (N=77), prediction was best (AUC=0.76, 95% CI: 0.65-0.87, $p=7.0\times10-5$) which yielded an optimal sensitivity of 0.96 with specificity of 0.94. Prediction was lowest in CC homozygotes (N=16) (AUC=0.60, 95% CI: 0.24-0.96, $p=0.50$). FIG. 9 shows the performance of the SKA2 prediction rule for PTSD for different genotypes groups. Even though the suicide prediction rule did not predict PTSD from baseline after exclusion of childhood trauma (AUC=0.48, 95% CI: 0.35-0.61), prospective changes in SKA2 methylation during deployment in interaction with genotype resulted in a significant prediction in absence of childhood trauma as a factor (AUC=0.69, 95% CI:0.55-0.82), indicating some utility in complete absence of recorded history.

Training a new PTSD prediction rule for the development of PTSD symptoms from baseline SKA2 methylation (N=93) showed that the development of PTSD symptoms is predicted fairly well in a model that included childhood trauma (AUC=0.85, 95% CI: 0.76-0.92, p<0.001), with an optimal sensitivity of 0.94 and a specificity of 0.70. A model that also included pre-deployment PTSD symptoms was slightly better (AUC=0.86, 95% CI: 0.79-0.94) while prediction of PTSD symptoms from baseline SKA2 methylation levels in a model without childhood trauma yielded less robust results (AUC=0.74, 95% CI: 0.64-0.84).

Discussion

This study provides converging evidence for a role of SKA2 methylation in stress-related psychopathology. Longitudinal decreases in SKA2 methylation after deployment were related to the development of PTSD symptoms, whereas exposure to deployment related traumatic stress was associated with increases in SKA2 methylation over time. In an independent sample, higher levels of SKA2 methylation were associated with a blunted cortisol stress response. These findings are consistent with an interpretation in which increases in SKA2 methylation after trauma reflects a functional adaptation of the physiological cortisol stress response. Conversely, unchanged or decreased SKA2 methylation may indicate persistence of a high cortisol stress response with the risk of exhaustion of the hypothalamic-pituitary-adrenal axis (HPA) and subsequent development of PTSD. Such a role of SKA2 would be in agreement with its importance for HPA-axis functionality as highlighted by studies showing that SKA2 knockdown affects glucocorticoid feedback inhibition (Rice et al. 2008), and the association of (epi)genetic variation in SKA2 with suppression of the cortisol awakening response (Guintivano et al. 2014). In addition to the longitudinal decrease in SKA2 methylation related to the development of PTSD symptoms, pre-deployment SKA2 methylation levels in concert with childhood trauma significantly predicted the development of PTSD symptoms. Validating a previously published SKA2 suicide prediction rule for PTSD using pre-deployment SKA2 methylation levels and childhood trauma resulted in a significant prediction of PTSD even when not taking trauma exposure during deployment into account (AUC: 0.66, p=0.011). This prediction was particularly significant in T allele carriers (N=77, AUC=0.76). The relevance of inclusion of childhood trauma in this model is in line with previous studies showing the effects of childhood trauma on hypothalamic-pituitary-adrenal (HPA) axis activity (Yehuda et al. 1991; Carpenter et al. 2007; Lovallo et al. 2012; Heim et al. 2000). A new predictor rule derived from the baseline SKA2 methylation that again included childhood trauma, also predicted PTSD symptoms with fairly good accuracy (AUC=0.85, p<0.001). These data suggest that SKA2 methylation together with childhood trauma maybe of use as a PTSD biomarker.

The observation that the prediction is superior in T allele carriers is difficult to interpret in light of the fact that DNA methylation changes occur on the C allele of the rs7208505 SNP. It is possible that the T allele marks some relevant functional change through a mechanism that remains to be determined. Previous studies have demonstrated that SNPs within PTSD-associated genes may alter the 3D structure and facilitate interaction of enhancer and promoter regions to drive transcription (Klengel et al 2013).

A similar mechanism may be at play for SKA2 at rs7208505 or SNPs in linkage disequilibrium with this locus. Of relevance, publically available histone H3 lysine 27 acetylation and H4 tri-methylation signatures implicate a possible enhancer region within a few kb upstream of rs7208505 on chr17 within a HapMap implicated LD block with rs7208505. Alternatively, Guintivano et al. (2014), originally reported an ENCODE implicated glucocorticoid receptor binding peak proximal to rs7208505 as well as one in the promoter region of SKA2. As this data was generated by immunoprecipitation for the glucocorticoid receptor following dexamethasone treatment, these two peaks may be an artifact of a single glucocorticoid receptor binding event occurring across three dimensionally folded DNA, further suggesting that genetic effects at rs7208505 may be mediating conformational changes to drive transcription of SKA2. However, these effects should be further investigated because at present they also may pose a chance finding in a small sample. One particular strength of the current study is the possibility to study SKA2 methylation in a longitudinal design before and after deployment. To our knowledge, the SKA2 biomarker in this longitudinal study represents the first genetic and epigenetic biomarker with potential for prospective prediction of PTSD. Association of the SKA2 methylation levels with the endocrine stress response in an experimental stress paradigm suggests that SKA2 indicates the actual and functional response to stress, which adds to the credibility of the SKA2 biomarker. In contrast to the documented strong influence of gender on cortisol stress responsivity that is thought to reflect physiological differences (Vinkers et al 2014), the absence of a direct mediating effect of SKA2 methylation levels for cortisol stress reactivity suggests that SKA2 may function as a stress responsivity biomarker rather than a direct causal link. SKA2 methylation does not explain (mediate) the effects of childhood trauma on stress responsivity. The association of SKA2 methylation with several other HPA-axis related symptoms such as depression, neuroticism and suicide is consistent with the central role of stress-induced alterations in HPA-axis reactivity in PTSD and many other disorders (Mehta and Binder 2012; de Kloet et al. 2006; Yehuda et al. 1991) and points to a role of SKA2 methylation as a general stress responsivity biomarker.

The results of this study should be interpreted in the context of its limitations. The longitudinal cohort included relatively small pre-selected groups, which precludes a meaningful analysis of positive predictive values. Additionally, our findings were obtained in male Caucasian individuals and it may therefore be difficult to directly extrapolate the findings to other samples and populations.

In conclusion, this longitudinal study shows that traumatic stress and PTSD have opposite effects on SKA2 methylation. Whereas traumatic stress exposure leads to increasing SKA2 methylation levels, the development of PTSD is associated with decreasing SKA2 methylation. The fair prediction of PTSD from pre-deployment SKA2 methylation levels in concert with childhood trauma as well as the association with HPA axis responsivity underscore the potential of SKA2 prediction. Together they provide a strong basis for further studies of genetic and epigenetic variation of SKA2 as a marker for stress susceptibility in general and for PTSD in particular.

Example 4

Stress/Anxiety Metric and Biomarker of Stress Response

Various psychological scales and or physiological metrics can be used as a 'stress' metric in the model. Suicidal ideation, anxiety, and stress metrics were obtained through different scales per cohort. For the GenRED offspring cohort, suicidal ideation and suicide attempt were derived from the Composite International Diagnostic Interview (CIDI) Suicidality Questionnaire. A positive anxiety metric was determined by a score of ≥25 on the Self-Report for Childhood Anxiety Related Disorders (SCARED) (Birmaher et al., 38(1) J. AM. ACAD. CHILD ADOLESC. PSYCHIATRY 1230-36 (1999)). For the prospective cohort, suicidal ideation was measured by numeric responses to question 10 of the Montgomery Asberg Depression Rating Scale (MADRS), anxiety was measured by numeric responses to question 4 of the Edinburgh Postnatal Depression Scale (EPDS) (Cox et al., 150 BR. J. PSYCHIATRY 782-86 (1987)), and perceived stress was measured by the total of the Perceived Stress Scale (PSS) (Cohen et al., 24(4) J. HEALTH SOC. BEHAV. 385-96 (1983)). Other studies demonstrate that levels of salivary cortisol may be good physiological indicators of perceived stress (Bougea et al., 9(2) EXPLORE (NY) 91-99 (2013)). This is not surprising given that cortisol response is a key glucocorticoid released in response to stress and activated by the hypothalamic pituitary adrenal (HPA) axis, the 'stress system' believed to be dysregulated in suicidal individuals. Suicidal individuals exhibit a reduced ability to suppress the experimentally administered synthetic glucocorticoid, dexamethasone (Coryell W. and Schlesser M., 158 (5) AM. J. PSYCHIATRY 748-53 (2001)), and the cortisol stress response has been identified as one of the most promising candidate suicide endophenotypes (Mann et al., 156(2) AM. J. PSYCHIATRY 181-89 (1999)). Other studies have demonstrated evidence that first degree relatives of suicide victims fail to mount a proper HPA axis response to stress (McGirr et al., 35(6) J. PSYCHIATRY 399-408 (2010)). Such findings are consistent with the diathesis-stress or dual risk hypothesis, whereby an underlying biological state moderates an aberrant response to stress Mann et al., 156(2) AM. J. PSYCHIATRY 181-89 (1999); Obradovic et al., 81(1) CHILD DEV. 270-89 (2010); Sameroff A., Developmental systems: contexts and evolution. *In Handbook of Child Psychology.* Wiley: New York. Vol 1, pp 237-94 (1983)).

Furthermore, a biomarker of stress response may function efficaciously to mark cortisol responsiveness and HPA axis function. Using our brain and peripheral genome-wide datasets in hand, we attempted to refine a biosignature of SKA2 interacting loci that may contribute to model prediction efficacy by acting as a proxy for current psychosocial stress. In other words, while SKA2 may represent a trait marker, the sought after biosignature represents the current state marker. We expect the combined knowledge of both vulnerability and current stress acting on the system to improve prediction accuracy for suicide attempt (SA) risk. Such a biosignature is desirable as it would eliminate the need to perform psychological assessments on potentially suicidal individuals who may not answer truthfully if secretly committed to a plan for suicide attempt. To accomplish this, we started in brain to identify those loci that significantly interact with SKA2 to associate with completed suicide in our FACs isolated neuronal dataset. We then assessed the ability of the most significant (nominally significant below P=0.0005, due to no FDR significance in these observations) loci to interact with SKA2 to predict suicidal ideation in peripheral blood from the GenRED offspring cohort with AUC metrics of greater than 0.8 (cut off for a 'good' biomarker) for SA in this training set. This resulted in a list of 72 probes for which we attempted to generate a consistent model of variance by taking the first Eigen vector (PC1) from a principle components analysis (PCA). Biosignature data from these probes from other datasets can then be input into the PCA trained in blood to generate a 'stress proxy' in alternative cohorts. In the GenRED offspring blood and saliva datasets and PPD blood based cohort, the PC1 metric demonstrated evidence for association to the proportion of granulocytes and monocytes present in the sample (Blood Rho=−0.68, p=0.0023; Saliva Rho=−0.62, p=0.004; PPD Blood Rho=−0.26, p=0.065) and resulted in significant predictions for SI that were significant after permutation testing (GenRED offspring Blood AUC=0.77, p=0.01, GenRED offspring Saliva AUC=0.81, p<2.1×10−16, prospective cohort blood AUC=0.88, p=0.03). In both the blood and saliva cohorts, the granulocyte and monocyte proportion demonstrated evidence for association to the AUC cortisol level (Blood Rho=0.43, p=0.075; Saliva Rho=0.45, p=0.056), suggesting suicide associated changes in cortisol facilitate a shift in the proportions of that peripheral immune cell type levels that are robustly detectable as a proxy of this change. To corroborate this finding, we assess the PC1 from the independent GTP cohort and found a significant association (GTP Rho=−0.11, p=0.049). Application of PC1 in the SKA2 based suicide prediction model was efficacious at predicting SA among the GTP cohort in individuals with PTSD with an AUC of 0.8. This strategy demonstrates an important starting point towards not only improving SA predictive models but in generating biosignatures that will help us to understand the peripheral and CNS based biology of suicidal behavior. The PCA trained on the GenRED offspring cohort is likely less robust than one we may generate by training on a larger cohort of individuals.

Example 5

Primers for SKA2 Promoter Regions

TABLE 13

SKA2 pyrosequencing primer sequences

| | Primer Name | Primer Sequence 5'-3' |
|---|---|---|
| SKA2 Promoter Region | SKA2 Promoter Region Forward Outside SKA2_Promoter_Fo1: | GAGGGGAAAGAAGGTGTGTT (SEQ ID NO: 11) |
| | SKA2 Promoter Region Reverse Outside SKA2_Promoter_Ro1: | CTACCCAATAAATCTCCTTCAC (SEQ ID NO: 12) |
| | SKA2 Promoter Region Forward Inside SKA2_Promoter_Fib1: | TGAAAGTAGAGAGGAGGGGG (SEQ ID NO: 13) |
| | SKA2 Promoter Region Reverse Inside SKA2_Promoter_Ri1: | TTTACACTCACCATCAATTCCAAC (SEQ ID NO: 14) |
| | SKA2 Promoter Region Pyrosequencing Primer 1 SKA2_Promoter_Pyro1: | AATGTGTTTTATGTAGAGG (SEQ ID NO: 15) |
| | SKA2 Promoter Region Pyrosequencing Primer 2 SKA2_Promoter_Pyro2: | GTTATTTAGTTTTTAATGGG (SEQ ID NO: 16) |
| | SKA2 Promoter Region Pyrosequencing Primer 3 SKA2_Promoter_Pyro3: | GTTGTTTAATGGAGGTTTTT (SEQ ID NO: 17) |
| | SKA2 Promoter Region Pyrosequencing Primer 4 | CCCATTAAAAACTAAATAA (SEQ ID NO: 18) |

TABLE 13-continued

SKA2 pyrosequencing primer sequences

| Primer Name | Primer Sequence 5'-3' |
|---|---|
| SKA2_Promoter_PyroR4: | |
| SKA2 Promoter Region Pyrosequencing Primer 5<br>SKA2_Promoter_PyroR5: | AACTATCACTCAACATCT<br>(SEQ ID NO: 19) |
| SKA2 Promoter Region Pyrosequencing Primer 6<br>SKA2_Promoter_PyroR6: | CATATTAAATAATTAACATTC<br>(SEQ ID NO: 20) |

In particular embodiments, CpGs within the SKA2 3'UTR, SKA2 upstream and/or SKA2 promoter regions can be used in the methods and compositions described herein. See Table 1. In a specific embodiment, PCR can be used to amplify the region of interest. In a more specific embodiment, PCR using nested primers can be used. In an even more specific embodiment, PCR primers can comprise SEQ ID NOS:11-12. In another embodiment, PCR primers can comprise SEQ ID NOS:13-14. In particular embodiments, SEQ ID NOS:11-14 can be used to amplify the SKA2 promoter region.

In another specific embodiment, PCR primers can comprise SEQ ID NOS:1-2. In another embodiment, PCR primers can comprise SEQ ID NOS:3-4. See Table 1. In particular embodiments, SEQ ID NOS:1-4 can be used to amplify the SKA2 promoter region. For SKA2 upstream, PCR primers can comprise SEQ ID NOS:6-7. Alternatively, the primers can comprise SEQ ID NOS:8-9. In further embodiments, SEQ ID NOS:6-10 can be used to amplify SKA2 upstream. See Table 1. The kit embodiments can comprise one or more of the above. Kit embodiments can comprise instructions for sample preparation, bisulfite conversion, PCR procedure/conditions, pyrosequencing and the like.

TABLE 14

PCR conditions can include, but are not limited to, the following:
Sample PCR Conditions

| 1. | 95° C. for 3:00 |
| 2. | 95° C. for 0:30 |

TABLE 14-continued

PCR conditions can include, but are not limited to, the following:
Sample PCR Conditions

| 3. | Annealing temp* for 0:30 |
| 4. | 72° C. for 0:30 |
| 5. | Go to step 2 for 39 more cycles |
| 6. | 72° C. for 5:00 |
| 7. | Hold at 4° C. |

In a specific embodiment, the annealing temp for the outside PCR is 59.4° C. and the inside PCR is 61.3° C. For the SKA2 3'UTR, the outside annealing is 59.3° C. and the inside is 60.5° C. See Table 1.

In further embodiments, sequencing can be performed using a primer shown in any one of SEQ ID NOS:15-20. In a particular embodiment, the primer shown in SEQ ID NO:18 is used. For the SKA2 3' UTR (see Table 1), SEQ ID NOS:1-2 can be used for outside PCR, SEQ ID NOS:3-4 can be used for inside PCR. In a specific embodiment, SEQ ID NO:5 can be used for sequencing. For SKA2 upstream (see Table 1), SEQ ID NOS:6-7 can be used for outside PCR, SEQ ID NOS:8-9 can be used for inside PCR. In a specific embodiment, SEQ ID NO:10 can be used for sequencing.

Accordingly, the methylation level of CpGs located within the SKA2 promoter (including the region amplified by the primers above (e.g., SEQ ID NOS:1-2, and/or SEQ ID NOS:3-4)) can be measured from DNA isolated from a sample collected from a subject. In addition, the methylation level of CpGs located upstream of the SKA2 3'UTR can be measured (including the region amplified by the primers above (e.g., SEQ ID NOS:6-7 and/or SEQ ID NOS:8-9).

We claim:

1. A method for treating post-traumatic stress disorder (PTSD) in a subject comprising the step of administering a PTSD treatment to a subject predicted to have PTSD using a method comprising the steps of:
   (a) measuring DNA methylation level of a CpG dinucleotide located on the minus strand of chromosome 17, at position 57187729 from DNA isolated from a sample collected from the subject;
   (b) detecting the genotype at the single nucleotide polymorphism (SNP) rs7208505, from DNA isolated from a sample collected from the subject; and
   (c) using a linear model that incorporates the measured DNA methylation level and genotype at rs7208505, age and sex to predict PTSD in the subject,
   wherein the PTSD treatment comprises psychotherapy, antidepressants and/or anti-anxiety medication.

2. The method of claim 1, wherein the linear model further utilizes a stress/anxiety metric.

3. The method of claim 2, wherein the stress/anxiety metric comprises the results from a stress/anxiety questionnaire.

4. The method of claim 2, wherein the stress/anxiety metric comprises salivary cortisol measured from the subject or a biomarker thereof.

5. The method of claim 1, wherein the sample is a blood, serum, or saliva sample.

6. The method of claim 1, wherein the sample is a blood, serum, or saliva sample taken before a stressor and then again after a stressor.

7. The method of claim 1, wherein a difference in DNA methylation at relative to a control is modeled with rs7208505 as an additive covariate to predict PTSD risk.

* * * * *